(12) United States Patent
Huang et al.

(10) Patent No.: US 11,497,637 B2
(45) Date of Patent: Nov. 15, 2022

(54) IMPLANTABLE DEVICES AND METHODS TO TREAT BENIGN PROSTATE HYPERPLASIA (BPH) AND ASSOCIATED LOWER URINARY TRACT SYMPTOMS (LUTS)

(71) Applicant: Prodeon, Inc., Taipei (TW)

(72) Inventors: Mark Huang, Pleasanton, CA (US); Kenneth Chih-Ping Chang, San Jose, CA (US); Jimmy Jen, Saratoga, CA (US); Yue-Teh Jang, Los Altos, CA (US); Thomas Hsu, Foster City, CA (US); Senzan Hsu, Foster City, CA (US); Kondapavulur T. Venkateswara-Rao, San Jose, CA (US)

(73) Assignee: Prodeon Medical Corporation, Taipei (TW)

( * ) Notice: Subject to any disclaimer, the term of this patent is extended or adjusted under 35 U.S.C. 154(b) by 17 days.

(21) Appl. No.: 15/972,031

(22) Filed: May 4, 2018

(65) Prior Publication Data
US 2018/0318114 A1      Nov. 8, 2018

Related U.S. Application Data

(60) Provisional application No. 62/502,056, filed on May 5, 2017.

(51) Int. Cl.
*A61F 2/04* (2013.01)
*A61F 2/90* (2013.01)
(Continued)

(52) U.S. Cl.
CPC .......... *A61F 2/90* (2013.01); *A61B 17/00234* (2013.01); *A61B 17/320725* (2013.01);
(Continued)

(58) Field of Classification Search
CPC ..................... A61F 2002/047; A61F 2002/048
See application file for complete search history.

(56) References Cited

U.S. PATENT DOCUMENTS

| 4,973,301 A | 11/1990 | Nissenkorn |
| 5,518,498 A | 5/1996 | Lindenberg et al. |

(Continued)

FOREIGN PATENT DOCUMENTS

| JP | H06-048674 U | 7/1994 |
| JP | 2008-515586 A | 5/2008 |

(Continued)

OTHER PUBLICATIONS

Instructions for Use: Cordis TrapEase Permanent Vena Cava Filter with the VisEase Angiographic Vessel Dilator. Jan. 2016. (Year: 2016).*

(Continued)

*Primary Examiner* — Leslie Lopez
(74) *Attorney, Agent, or Firm* — Dergosits & Noah LLP; Todd A. Noah

(57) ABSTRACT

The invention is devices and methods to treat benign prostatic hyperplasia (BPH) and associated lower urinary tract symptoms infections (LUTS). The devices are intra-urethral implants placed in a patient in need thereof by minimally invasive procedures, preferably under local anesthesia in an office environment. The devices are sized and designed for atraumatic insertion and expansion within the urethra to engage and retract enlarged prostatic tissue proximate to the urethra that is leading to adverse symptoms associated with BPH. The methods include steps to deploy the implant devices of the invention using a delivery system of the invention and at target prostatic tissue that is visualized during the procedure and yields a reduction in the symptoms of BPH.

13 Claims, 17 Drawing Sheets

(51) Int. Cl.
   *A61B 17/00* (2006.01)
   *A61B 17/3207* (2006.01)
   *A61F 2/962* (2013.01)
   *A61F 2/86* (2013.01)
   *A61M 27/00* (2006.01)
   *A61B 17/3209* (2006.01)
   *A61F 2/95* (2013.01)

(52) U.S. Cl.
   CPC ............ *A61F 2/04* (2013.01); *A61F 2/86* (2013.01); *A61F 2/962* (2013.01); *A61B 17/3209* (2013.01); *A61B 2017/00274* (2013.01); *A61B 2017/32096* (2013.01); *A61F 2002/047* (2013.01); *A61F 2002/9528* (2013.01); *A61F 2220/0008* (2013.01); *A61F 2230/001* (2013.01); *A61F 2230/0073* (2013.01); *A61M 27/008* (2013.01)

(56) References Cited

U.S. PATENT DOCUMENTS

| | | | | |
|---|---|---|---|---|
| 5,830,179 | A * | 11/1998 | Mikus | A61F 2/04 604/517 |
| 8,801,746 | B1 * | 8/2014 | Kreidler | A61B 17/1215 606/200 |
| 9,848,905 | B2 | 12/2017 | Kilemnik | |
| 2005/0015111 | A1 * | 1/2005 | McGuckin, Jr. | A61F 2/01 606/200 |
| 2005/0038470 | A1 * | 2/2005 | van der Burg | A61B 17/0057 606/213 |
| 2005/0119721 | A1 | 6/2005 | Rabkin et al. | |
| 2007/0156225 | A1 | 7/2007 | George et al. | |
| 2009/0156977 | A1 * | 6/2009 | Daignault | A61F 2/04 604/8 |
| 2009/0306703 | A1 * | 12/2009 | Kashkarov | A61F 2/0105 606/200 |
| 2010/0274346 | A1 | 10/2010 | Chouinard et al. | |
| 2011/0077676 | A1 | 3/2011 | Sivan et al. | |
| 2011/0276081 | A1 * | 11/2011 | Kilemnik | A61B 17/320725 606/198 |
| 2012/0191174 | A1 | 6/2012 | Vinluan et al. | |
| 2013/0268053 | A1 * | 10/2013 | Molaei | A61B 17/12118 623/1.15 |
| 2014/0188205 | A1 | 7/2014 | Andreas et al. | |
| 2015/0223953 | A1 * | 8/2015 | Pendleton | A61F 2/852 623/23.68 |
| 2015/0257908 | A1 | 9/2015 | Chao et al. | |
| 2016/0015394 | A1 | 1/2016 | Cedro, Jr. et al. | |
| 2016/0015507 | A1 * | 1/2016 | Johnson | A61B 90/39 606/200 |
| 2017/0000598 | A1 | 1/2017 | Bachar | |
| 2017/0065406 | A1 | 3/2017 | Calomeni et al. | |
| 2017/0135830 | A1 * | 5/2017 | Harkin | A61B 1/307 |
| 2018/0185183 | A1 | 7/2018 | Christakis et al. | |
| 2018/0318114 | A1 | 11/2018 | Huang et al. | |
| 2019/0038443 | A1 | 2/2019 | Sicotte et al. | |
| 2019/0083261 | A1 | 3/2019 | Perszyk et al. | |

FOREIGN PATENT DOCUMENTS

| | | |
|---|---|---|
| KR | 10-1502956 | 3/2015 |
| WO | 2008086195 | 7/2008 |
| WO | 2015/111063 A1 | 7/2015 |
| WO | 2015/153507 | 10/2015 |
| WO | 2017/017499 A1 | 2/2017 |
| WO | 2017/081326 A1 | 5/2017 |
| WO | 2017/112856 A1 | 6/2017 |

OTHER PUBLICATIONS

International Search Report and Written Opinion for International Application No. PCT/US18/31250, dated Jul. 27, 2018.
International Preliminary Report on Patentability in International Patent Application No. PCT/US2018/031250, dated Nov. 5, 2019.
International Search Report and Written Opinion from related International Patent Application No. PCT/US20/55067, dated Jan. 29, 2021.
Storz, Karl, "Extract from the Pediatric Surgery Catalog Urology," available: https://www.karlstorz.com/cps/rde/xbcr/karlstorz_assets/ASSETS/3597875.pdf, retrieved Jun. 4, 2021.
European Search Report in European Patent Application No. 18794309, dated Dec. 18, 2020.
Search Report from corresponding Japanese Patent Application No. 2019-560245, dated Oct. 6, 2021.
Notice of Reasons for Refusal from corresponding Japanese Patent Application No. 2019-560245, dated Oct. 8, 2021.

* cited by examiner

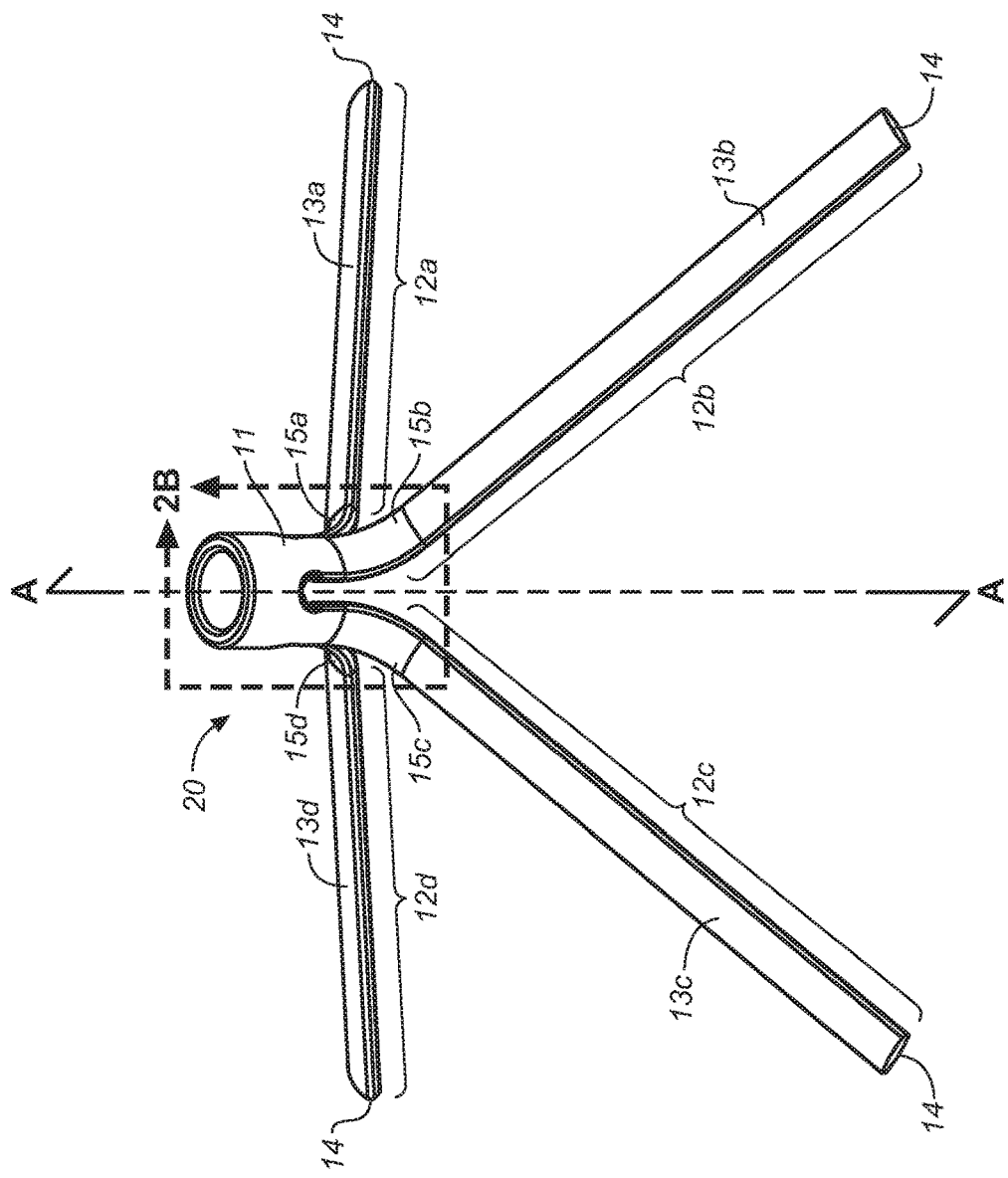
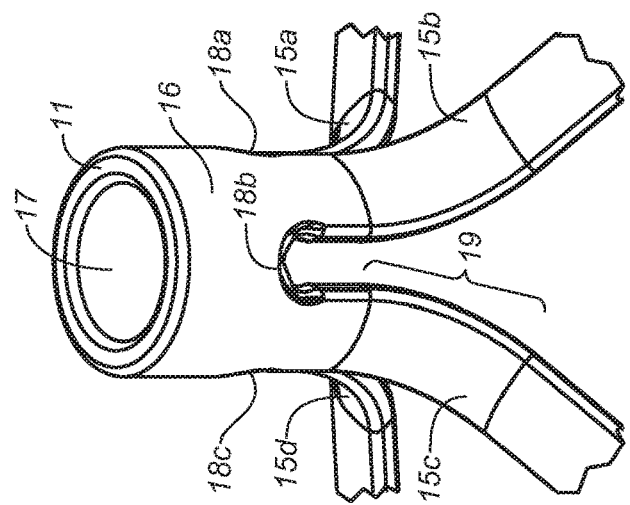
FIG. 2A
FIG. 2B

IMPLANTABLE DEVICES AND METHODS TO TREAT BENIGN PROSTATE HYPERPLASIA (BPH) AND ASSOCIATED LOWER URINARY TRACT SYMPTOMS (LUTS)

CROSS REFERENCE TO RELATED APPLICATIONS

This application claims priority to U.S. Provisional Application 62/502,056, filed May 5, 2017. The priority of this application is expressly claimed, and the disclosure is hereby incorporated by reference in its entirety.

BACKGROUND OF THE INVENTION

The prostate is a walnut-shaped gland that wraps around the urethra through which urine is expelled from the bladder and plays a crucial role in the reproductive system of men. Although the gland starts out small, it tends to enlarge as a man ages. An excessively enlarged prostate results in a disease known as benign prostatic hyperplasia (BPH). Benign prostatic hyperplasia (BPH) refers to the abnormal, but non-malignant (non-cancerous) growth of the prostate observed very commonly in aging men. BPH is a chronic condition and is associated with the development of urinary outflow obstruction in the prostatic urethra. It also causes a range of disorders referred to collectively as Lower Urinary Tract Symptoms (LUTS), including sexual dysfunction, frequent urination, difficulty in voiding urine, urinary retention, urinary leakage, and urinary tract and bladder infections that worsen as the abnormal growth in the prostate enlarges and progresses.

BPH presents as an age-related phenomenon in men, typically starting as early as 40 years of age. The prostate goes through two main growth periods over time. The first occurs in puberty, when the prostate doubles in size. The second phase begins around age 25 and continues irregularly thereafter. BPH often begins to develop during the second growth phase, and as the prostate enlarges, the gland presses against and impinges the urethra. The prevalence of BPH, which has been examined in several studies around the world, is approximately 10% for men in their 30s, 20% for men in their 40s, reaches 50% to 60% for men in their 60s, and is 80% to 90% for men in their 70s and 80s. At some time, almost all men will develop some pathological features consistent with BPH. As of 2015, over 15 million men in the United States exhibited symptoms of BPH.

Combined with a tendency of the bladder wall to become thicker and weaker, BPH patients lose the ability to completely empty the bladder. Urethral narrowing and urinary retention cause many of the problems experienced by BPH patients.

Most BPH patients are treated either by medication or surgery to restore the ability of urine to pass through the urethra proximate to the prostate gland. Alpha-Blockers are the most common drugs prescribed for BPH. They act against the dynamic component of urinary outflow obstruction by relaxing smooth muscles in the bladder neck, prostate capsule, and prostatic urethra. 5-alpha-reductase inhibitors (5-ARIs) are more effective in men with large prostates. They act by reducing the prostate gland size. While these drugs provide some relief from BPH, they have unavoidable side effects and do not offer a complete solution for many BPH patients. Side effects include orthostatic hypotension, dizziness, decreased libido and sexual dysfunction (e.g., erectile dysfunction, ejaculatory dysfunction and retrograde ejaculation). Other BPH patients do not experience significant alleviation of symptoms, and many find the requirement for daily medication both bothersome and costly.

Surgical procedures provide BPH relief by removing a significant portion the prostate tissue. Several traditional surgical procedures are available, all of which require hospitalization and some form of spinal, epidural, or general anesthesia. Transurethral resection of the prostate (TURP) is the main surgical treatment for BPH and remains the gold standard against which other treatments are compared. Traditional surgical techniques differ in the location of the incision made by the surgeon to access the prostate and in the method by which prostatic tissue is removed. For example, some surgeries use laser energy, heat, or radio frequency to remove tissue from the prostate. They include laser enucleation, photoselective vaporization (PVP), transurethral needle ablation (TUNA) using radiofrequency energy, transurethral microwave thermotherapy (TUMT) and transurethral incision of prostate (TUIP). However, these traditional surgical approaches to the treatment of BPH are invasive, non-reversible, and have significant drawbacks including the placement of a temporary catheter for a few months, risk of infection, loss of sexual function, urinary incontinence, and restenosis—wherein recurring hyperplasia of cells in the prostate regrow to cause a recurrence of the narrowing of the urethra opening and also a recurrence of the LUTS symptoms described above.

Although removing prostatic tissue relieves some BPH symptoms, tissue removal by traditional surgical approaches is irreversible and any adverse effects of the surgery may afflict the patient for life or affect the patients' quality of life. Moreover, surgical approaches are associated with the inherent risks from the surgery itself, risk recurrence from the regrowth of removed prostatic tissue, and, depending on the extent of the disease and the particular surgical approach necessary for an individual patient, can require recovery periods as long as 3 to 6 weeks.

Because of the recognized drawbacks of traditional surgery, less invasive therapies have been developed and, depending on the extent of disease, may be chosen by patients and their physicians as an alternative to lifelong medication or surgery. These less-invasive therapies may be suited for those patients not willing or medically not fit to have a surgical procedure performed under general anesthesia.

Less invasive techniques include transurethral methods that actually remove enlarged prostatic tissue, including electrovaporization where an urologist inserts a tube-like instrument called a resectoscope through the urethra to reach the prostate. An electrode attached to the resectoscope moves along the urethra and adjacent to the enlarged prostatic tissue while transmitting an electric current that vaporizes the targeted tissue.

In water-induced thermotherapy, an urologist passes heated water through a catheter inserted into the urethra. First, a treatment balloon is placed in the urethra, roughly in the middle of the prostate. Then, super-heated water flows through the catheter into the treatment balloon, which heats and destroys the surrounding prostate tissue.

In transurethral needle ablation, an urologist inserts a cystoscope through the urethra to the prostate and then inserts small needles through the end of the cystoscope into the prostate. The needles send radiofrequency energy that heats and destroys selected portions of prostate tissue.

In transurethral microwave thermotherapy, a catheter is inserted down the urethra and delivers microwave energy to heat and destroy prostate tissue. The temperature becomes high enough inside the prostate to destroy enlarged tissue.

In high-intensity focused ultrasound therapy, an urologist inserts a special ultrasound probe into the rectum, near the prostate. Ultrasound energy waves from the probe heat and destroy enlarged prostate tissue.

While these less invasive techniques are generally less traumatic than traditional surgery, each destroys prostatic tissue and is irreversible. To avoid destroying the prostatic tissue, other therapeutic procedures have been developed that are designed to enlarge the diameter of the prostatic urethra without actual removal of tissue from the prostate gland.

In one technique called "Urolift," an urologist inserts the Urolift device through a standard rigid cystoscope and determines the areas of the prostate gland that are significantly enlarged. Once the desired location has been identified, urologist deploys the Urolift implant. The Urololift device inserts a small needle through the width of the prostate gland to place an anchor on the far side of the prostate. Then, the suture is tightened to forcefully retract prostatic tissue surrounding the urethra and open the prostatic urethra. The urologist can place several implants and sutures in this manner along the length of the urethra, and the total number of implants and sutures varies, depending on the size, shape and length of the obstructive tissue.

Other procedures rely on an implantable device placed within the prostatic urethra that is designed to enlarge the diameter of the urethra. A prostatic implant involves a procedure wherein the urologist inserts a small device within the prostatic urethra which is narrowed by enlarged prostatic tissue. Once in place, the implant is designed to help keep the urethra open, while preventing enlarged prostate tissue from total impingement or narrowing of the urethra. Ideally, prostatic implants eliminate the need to surgically remove prostatic tissue and are expected to reduce the risks of infection, sexual dysfunction, and incontinence, inherent and traditional to even less-invasive, surgical approaches. The procedure is also considered reversible since the implants may be removed and additional surgical treatments may be performed in the future.

Several different designs for intra-prostatic implants or urethral stents have been developed. In one design, a cylindrical tubular mesh is compressed to a reduced size, inserted through the urethra to the location of the enlarged prostate and allowed to expand to increase the diameter of the urethra. While such mesh-style apparatus does not destroy prostate tissue, they have a tendency to migrate within the urethra and into the urinary bladder. Also, when such implants extend into the bladder—either by design or by intra-urethral migration—the implants can become encrusted with cells and mineralization from urine present in the bladder. To avoid the migration issue, other implant urethral stent designs are fixed to the walls of the urethra using different anchoring features. These designs have the drawback of disrupting the epithelial layer of cells on the interior of the urethra, causing injury to the urethral wall and risking bleeding, infection, hematuria, abnormal tissue growth, formation of stones or other trauma around the point of attachment of the implant to the urethral wall. Mesh-like urethral stent designs also have the disadvantage of having a high implant surface area relative to the prostatic tissue area over which they apply their expansion or retraction force. Higher implant mass and higher implant surface area are desirable to provide sufficient retraction forces to push the hyperplastic lobes outward and expand the lumen of the prostatic urethra. Too high a retraction force may cause significant pain to the patient and damage the urethral wall. Higher implant surface area also increases the probability for encrustation and stone formation on the surface of the implant over time, thereby causing either urethral narrowing or structural degradation of the implant. It is therefore desirable to design an optimal implant with sufficient "retraction force" or "radial force" or "expansion force" to push out the hyperplastic tissue of the prostate and increase the lumen of the prostate and provide LUTS relief using minimal implant surface area and/or implant mass. The present invention describes implant designs with low surface area ratio relative to the prostatic tissue area that they treat to minimize encrustation and stone formation, while providing effective expansion force to open the lumen of the prostatic urethra.

Other implant designs rely on an expandable structure that rests in the three grooves formed between two lateral and the medial lobes of the prostate. The design and manufacturing strategy for an intra-urethral prostatic implant, together with its deployment strategy, accompanying deployment system, and ability to retrieve the implant are particularly important because a number of necessary, and potentially conflicting, design criteria must be met. An ideal implant design facilitates deployment in an office-based procedure that does not involve the drawbacks and potential complications of traditional surgical techniques and does not require hospitalization or general anesthesia. The implant should be easy to deliver and to retrieve using conventional companion or ancillary devices such that practicing urologists are familiar with the apparatus necessary to deliver the device. The design should be compatible with companion urology devices used to diagnose BPH and image the urethra, bladder and other anatomical and physiological features of the urinary system.

Additionally, the design of the implant must account for the unique physiology of the prostate gland. The prostate is made up of two larger lateral lobes and a medial lobe that are joined together along the length of the urethra and that surround the urethra on all sides. Particularly as the prostate tissue expands in a hyperplastic condition, grooves are formed along the length of the boundary between the lateral lobes of the prostate or between either lateral lobe and the medial lobe. The design of an implant should result in exertion of force directly on the lobes of the prostate tissue immediately proximate to the urethra and retract prostatic tissue along a length thereof to restore the patency of the urethral passageway. Preferably the device is spaced away from the grooves formed along the length of the contact between adjacent lobes of the prostate and does not migrate during the implantation period, while preserving normal urological and sexual function. The implant should also be designed to be placed between the bladder neck opening and the external urinary sphincter, without causing undue trauma to the urethra, bladder neck and the external sphincter. And more preferable, the device must be placed between the bladder neck and the verumontanum to prevent irritation of the bladder neck and obstruction of the ejaculatory ducts, respectively.

All of the implants described above including the Urolift implants are placed using rigid metallic sheaths and rigid endoscopes that have a large diameter (22 F and above or 7 mm) used in urological procedures. Inserting the rigid sheaths and endoscopes (or cystoscopes) through the penis into the prostatic urethra could be very painful. General or local anesthesia is required to place these implants in the prostatic urethra. Therefore, there is a need to design flexible systems that are compatible with flexible sheaths and flexible endoscopes used in interventional urological procedures. In addition, there is a need to reduce the diameter (or profile) of the implant and delivery systems so that the procedures may be done in an office setting using flexible cystoscopes, without the need for anesthesia. Also, the delivery and deployment of the implants described above, may be challenging since they could obstruct direct visualization of the urethra during device placement. As such, there is an additional need to design the implants and delivery systems that allow for direct visualization during advancement of the delivery system and placement of the implant in the prostatic urethra.

It is also desirable to have features on the implant and delivery system to reposition the implant in the event that it is misdeployed. Features to hold the device and reposition the devices, using traditional graspers or other ancillary devices to retrieve stones during urological procedures, in conjunction with imaging using an endoscope or cystoscope are needed.

Finally, it is desirable for the implant to be retrievable at the discretion of the urologist, patient symptoms after treatment, and patient condition after relief of BPH symptoms. So, the design of the implant must facilitate simple and atraumatic removal in an outpatient environment, in the physician's office without the need for hospitalization. In some cases, the implant may be retrieved after a pre-specified implantation period and replaced by a fresh, new implant to treat BPH.

BRIEF SUMMARY OF THE INVENTION

The invention is devices and methods of treatment and device manufacturing to provide an implant and delivery system for the treatment of urinary outflow obstruction symptoms and lower urinary tract symptoms associated with or caused by or secondary to benign prostatic hyperplasia. The implant is designed to satisfy several performance and operational criteria to overcome challenges in the treatment of BPH. The implant is adaptable for the range of potential prostate sizes, lengths and tissue morphologies that may be encountered in the adult male population. The implant is designed to resist migration due to urethra flow dynamics and movement once it is placed at the target site. The implant is also configured to permit placement and recovery using minimally invasive procedures using a flexible endoscope under local anesthesia (or topical anesthesia or no anesthesia). The implant is designed with minimal mass and surface area to prevent encrustation, while providing sufficient retraction force to push open the narrowing of the prostatic urethra. The implants are sized and shaped to be delivered and retrieved in a compressed configuration through traditional diagnostic imaging and delivery systems, such as traditional flexible cystoscopes used for urological procedures and that are used here to permit the delivery, visualization, deployment, and retrieval of the implant.

The implant performance criteria include expansion with sufficient force to engage and or retract tissue at the lobes of the prostate, and depending on the specific physiology of a patient, engage and displace the lobes of the prostate, thereby increasing the diameter of the urethra for urinary flow. The design of the device should reduce the potential for migration and must be configured so that it does not extend beyond the external urinary sphincter and bladder neck. Although the implant may be susceptible of being placed permanently for the life of the patient, it is also desirable for the implant to have structural features to facilitate retrieval with minimal or no tissue damage, if additional treatments, such as replacement with a new implant, a different device, or surgery, are needed.

Methods for deployment and retrieval of the implant through a cystoscope under direct visualization, include retrieval and removal within one month to many years after implantation. The overall configuration of the device facilitates atraumatic removal through a catheter or a sheath into which the implant is contained by collapsing the implant to a reduced diameter and confining the implant at the distal end of a catheter, sheath, cystoscope or endoscope channel for atraumatic removal. The structural profile of the implant and delivery system design minimizes bleeding, swelling, spasm, or injury to the urethra during placement, while restoring urinary function, and eliminating the future risk of pain, sexual dysfunction, or urinary dysfunction. The design of the delivery system includes visible marking to allow the user to place the implant at a precise location relative to anatomical landmarks within the urethra. Such visible markings include marker bands, notches, color identification, graduated edges, diametrical changes on the delivery system. The design and placement of the device does not interfere with urinary function (prevents incontinence and facilitates urination upon activation of the external sphincter). The design and placement method also minimizes the potential for migration of the implant along the urethra and towards the bladder or towards the penis.

The implant exerts an expansion or tissue retraction force greater than 0.5N, or preferably greater than 2N, and most preferably between 5 and 30N along a substantial portion of the length of the implant, counteracting the compression forces directed radially and constricting the lumen along the urethra by the enlargements of prostatic tissue. Because the prostate has three lobes and is asymmetric, the implant preferably has 2 or 4 or more tissue-engaging regions such that the tissue contacting regions are not disposed within the three grooves formed by adjacent lateral and medial lobes of the prostate. If the design has 3 tissue engaging regions, the design is preferable asymmetric relative to the prostate physiology such that the implant is not disposed in the interlobular grooves. Instead, the tissue-engaging regions of the implant directly engage each of the three lobes of the prostate along the length for retracting the enlarged tissue to relieve and expand the fluid communication capacity or lumen of the urethra. Visual markings, such as marker bands, notches, coloration, etching, surface finish variations may be placed on the expander to facilitate visualization and accurate placement or deployment of the implant in the urethra.

The implant fits within a delivery system having an outer diameter (OD) less than 18 French (1-6 millimeters) and is compatible with the working channel of rigid cystoscope or a flexible cystoscope that may have a diameter of 7 French (1.5-3 millimeters). The delivery system is able to advance with minimum resistance through the working instrument channel of the endoscope or cystoscope. In addition, the delivery system also incorporates sufficient free lumen to allow sufficient saline irrigation for sailing flow or fluid flow, typically with a minimum flow rate of 0.25 mL per second for direct visualization of the urethra during implant advancement and placement. The delivery system has a working port to connect to the irrigation source. In a preferred embodiment, the implant is confined in a collapsed configuration at the distal end of a delivery catheter having a soft tip for atraumatic deployment of the implant. The delivery system is capable of being traversed by a guidewire having a soft tip at the most distal end and by a mandrel or pusher ending just proximal of the implant.

In another embodiment, imaging elements are integrated into the delivery system. The imaging elements are compatible with existing video display systems made by Olympus, Stryker and Karl-Storz. The overall system profile is less than 26 F (9 millimeters), or more preferably between 17-12 F (6 millimeters) or smaller, to further minimize the pain during delivery and placement of the implant. Moreover, the integrated delivery system incorporating the implant and imaging elements may be a single-use or disposable medical device as compared to embodiments that are inserted through flexible and rigid cystoscopes that are resterilized and reusable.

The methods of the invention include methods of treatment of benign prostatic hyperplasia by implantation, and optionally subsequent retrieval, of any of the implant designs disclosed herein. All of the embodiments of the implant are designed to be maintained in a compressed configuration at the distal end of a delivery system. In one embodiment of a method for deployment, the implant is partially deployed, for example by transforming or partially relaxing from a completely collapsed to a partially expanded configuration, followed by additional manipulation of the delivery system to position the implant within the prostatic urethra, followed by completing the deployment step by causing the implant to assume the fully expanded configuration. Partial deployment may be achieved by preloading the cystoscope and implant into a sheath, with the implant adjacent to the distal tip of the cystoscope. The preloaded assembly of the sheath, cystoscope and implant are advanced through the urethra and once the desired position is reached, the implant is placed in position by pushing the implant proximally from the distal end of the cystoscope.

The method for implantation includes optionally performing a diagnostic cystoscopy to determine the length of the prostatic urethra from the verumontanum to the bladder neck, followed by determining the diameter of the urethra and selection of an appropriately sized implant based, at least in part, on the diameter of the selected implant of the invention, which may be measured by the diameter of opposing tissue-engaging regions of the implant in the expanded configuration. Diagnostic measurements of urethra length may also be obtained using abdominal ultrasound or trans-rectal ultrasound imaging methods. Measurement of urethra length from the bladder neck to the external sphincter may also be used to determine the appropriate implant size. In one deployment method, the clinician selects an implant having a pre-designated size that is maintained in a collapsed configuration at the distal end of the delivery system. The appropriately sized implant contained within the delivery system is introduced into the working channel of the cystoscope. The distal end of the delivery system is advanced, preferably under direct visualization, so that the distal end of the delivery system is proximal to the verumontanum for deployment. The staged deployment also includes a partial deployment of the implant in stages, such as by selected, partial withdrawal of the outer sheath of a delivery system to an intermediate position, preferably followed by verification of the size and position and orientation of the implant at the target site within the prostatic urethra. Further retraction of the outer sheath completes the deployment in a multi-step process that avoids inadvertent or misplaced deployment of the implant, which can be irreversible and require removal of the implant and the delivery system assembly. To improve implant deployment accuracy, it is also conceivable to engage the implant to the delivery system after the implant has expanded within the prostatic urethra. The delivery system would still be connected to the implant allowing the user to position the implant via the delivery system. Once the user is satisfied with the implant position, a release mechanism as described below may be triggered by the user to completely release the implant from the delivery system.

A modified version of the delivery system of the invention includes a delivery catheter having a braided reinforced sheath having a soft tip and designed to be traversed by a flexible tether wire having a fixture at the distal end thereof for preventing implant migration when deploying and converting the implant from the collapsed to the expanded configuration. Similarly, a dedicated catheter can be used for retrieval of the implant from within the prostatic urethra. Under such circumstances, retrieval is advantageously achieved by a tether wire having a specially designed distal tip that projects from the distal end of a retrieval catheter. A region of the retrieval tether wire has a shape memory property such that the tether loops back on itself to make an open-loop having a width smaller than the cross-section of the diameter of implant. Retrieval is achieved by extending the distal end of the tether wire through an open structure of in the solid body of the implant, forming a loop with the distal end of the tether wire around the implant, and using the tether wire to withdraw the implant back into the retrieval catheter and collapsing the implant to a reduced diameter for withdrawal from the prostate.

The structure on the implant itself that is engaged by the distal end of the tether wire can be a fixture dedicated for retrieval of the implant or can simply be any solid section of the implant, including the arms, that can be grasped by the tether wire. Specially designed retrieval catheters can also perform the function of the retrieval wire, are known and can be substituted at the selection of the clinician. This can be accomplished by a snare, collar, or other mechanical expedient that is used to pull the implant within the distal end of the removal sheath, collapsing the three-dimensional structure to fit in the distal end.

Finally, because the integrated device and delivery system are achieved with common surgical instruments, specifically with standard cystoscopes used with other urologic procedures, the implant can be placed and retrieved by an urologist without specialized equipment and under local anesthesia in an office environment and on an outpatient basis.

The methods of the invention include placement of the devices described herein within the urethra proximate to the prostate and below the bladder neck, including at specified distances between the bladder neck opening and external urinary sphincter. The methods include orienting the distal tip of a delivery system within the prostate and incrementally deploying the implant from a compressed to an expanded configuration such that deployment of the implant may be interrupted between expansion of the implant from the compressed to the expanded configuration in order to reorient or relocate the implant along the length of the urethra within the prostate. The methods also include orienting the device such that the contact regions of the implant engage a portion of the prostate away from the 3 apexes formed by the adjoining lobes of the prostate and to engage prostate tissue at a point spaced away from each apex.

Accordingly, the method includes visualization of the prostate lobes and respective apices during implantation and orientation of the implant using the delivery system to specifically engage portions of prostate tissue by the device to place the implant into the desired configuration. The ability to incrementally deploy the implant via manipulation of the delivery system allows precise placement and orientation of the implant relative to all of the physiological structures along the length of the urethra within the transition (or T)-zone of the prostate and preferably distal to the bladder neck without obstructing the verumontanum. The method also includes the deployment of a plurality of implants selected and sized for the physiological condition of a particular BPH patient, including, the selective deployment of dissimilar embodiments of the invention as described herein and in the accompanying Figures.

The methods include placement or removal of the implant device under local anesthesia, topical anesthesia or no anesthesia, using both flexible and rigid cystoscopes using the delivery systems described herein, together with visualization and accompanied by irrigation as described below. The methods also include atraumatic removal of the device without injury to the urethra and, optionally, placement of a replacement implant.

BRIEF DESCRIPTION OF THE DRAWINGS

FIG. 1 shows the placement of one embodiment of the implant from the present invention disposed in the prostatic urethra and engaging prostatic tissue on either side thereof between the bladder neck opening and the verumontanum.

FIGS. 2A-2C are perspective views, respectively, of an embodiment of the invention having a terminal hub at one end and a plurality of extensions or "arms" extending from the terminal hub to deploy a tissue-engaging region of the implant. Each tissue-engaging region originates at the hub, proceeds from the hub through a transitional region, and terminates at an atraumatic end. In the embodiment of FIG. 2A the arms are substantially linear across their length, while in the embodiment of FIG. 2C the arms are comprised of two curves that form linear tissue-engaging regions at the distal end of each arm. The structures that engage the prostatic tissue have been variously referred to as "legs,", "limbs", "extensions," and "arms" among other terms. For consistency in this specification, the term "arms" is used throughout. FIG. 2B is a hub showing detail of the structure thereof, including an optional internal space comprising a housing as well as integral transitional structures that connect to the hub to the arms.

FIG. 3A illustrates arms that are curvilinear across substantially in entire length thereof between the hubs. FIG. 3A features an attachment structure both proximal and distal to each hub for ease of deployment, and particularly, for retrieval. FIG. 3B-3D are embodiments having a substantially linear length of the tissue-engaging portion centrally located along the length of the arms can connecting the proximal hub and the distal hub. FIG. 3D shows a spiral configuration.

FIG. 11A shows the implant of the invention in a compressed shape at a distal end of the delivery system. FIG. 11B shows an initial stage of the deployment of the implant of the invention wherein the implant is in a partially expanded configuration. FIG. 11C shows a complete expansion of the implant from the compressed configuration and deployed at a target site in the expanded configuration outside the delivery sheath.

DETAILED DESCRIPTION OF THE INVENTION

Figure 1:
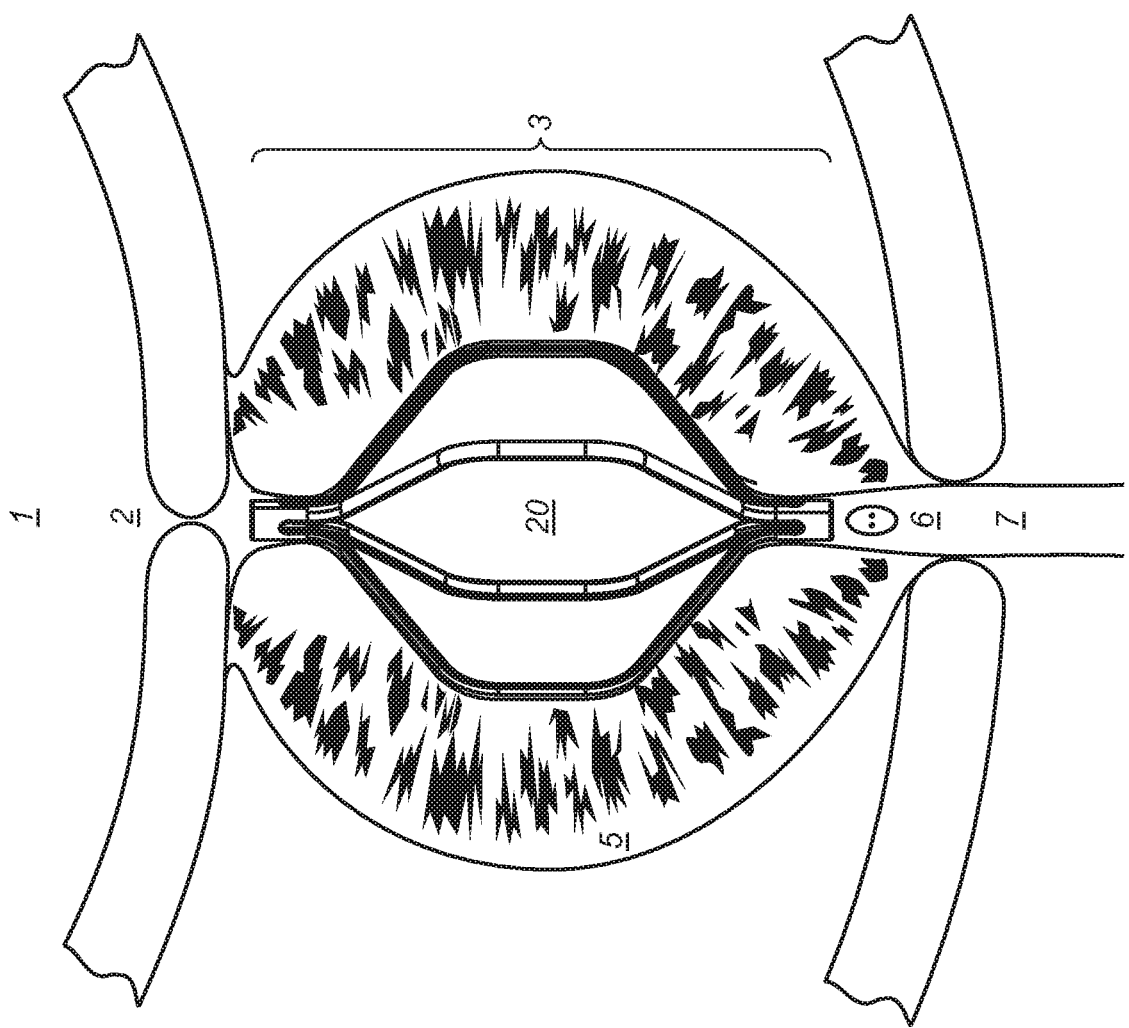
FIG. 1 is a cross-section of the male anatomy comprising the lower portion of the bladder, and the prostatic urethra in a physiological configuration typical of a patient suffering from BPH.

Definitions: The terms "therapeutically effective displacement" or "therapeutically effective retraction" or "therapeutically effective expansion", are used interchangeably herein and refer to an amount of displacement of prostatic tissue proximate to a restricted area of a urethra sufficient to increase the urethral lumen and treat, ameliorate, or prevent the symptoms of benign prostatic hyperplasia (BPH) or comorbid diseases or conditions, including lower urinary tract symptoms (LUTS), wherein the displacement of prostatic tissues exhibits a detectable therapeutic, prophylactic, or inhibitory effect. The effect can be detected by, for example, an improvement in clinical condition, or reduction in symptoms or absence of co-morbidities. Examples of clinical measures include a decrease in the international prostate symptom score (IPSS), reduction in post-void residual (PVR) volume of urine in the bladder after relief or increase in the maximum urinary flow rate (Qmax) or improvement in quality of life (QoL), improvement in sexual health (sexual health inventory for men or SHIM score) after treatment. The precise distance or volume of the displacement of prostatic tissue will depend upon the subject's body weight, size, and health; the nature and extent of the enlarged or diseased prostatic condition and the size of the implant selected for placement in the patient.

As used herein, a patient "in need of treatment for BPH" is a patient who would benefit from a reduction in the presence of or resulting symptoms of enlarged prostatic tissue caused by a non-malignant enlarging of the prostate gland and related disorders, including LUTS, urinary outflow obstruction symptoms and luminal narrowing of the prostatic urethra. As used herein, the terms "implant" or "expander" or "device" refer to the prosthetic device that is implanted within the prostatic urethra to relieve LUTS associated or caused by BPH.

As used herein, the terms "tissue engaging" with regard to an arms or extension of the structure of the implant refers to a length of the physical structure of the implant that engages prostatic tissue along the main portion of the lobes of the organ compressing on the urethra and restraints the tissue from further impingement on the patency of the urethra. "Tissue retracting" refers to the ability of the structure of the implant to exert the requisite force to displace tissue away from the compressed or narrowed urethra. The requisite force could be supplied by the inherent structure of the implant or by the expansion of the implant from the compressed to the expanded configuration, particularly where the implant is fabricated from a shape-memory or superelastic material having a predetermined expanded configuration designed to engage the hyperplasic prostate tissue and exert the requisite force. The length of a tissue-engaging or tissue-retracting structural feature in contact within these definitions is spaced away from the intra-lobular grooves that run along the length of the prostate surrounding the urethra and requires contact with a length of tissue along the length of the two lateral or lateral and medial lobes.

With respect to orientation of the various structures and anatomical references described herein, the term "proximal" and "distal" are relative to the perspective of the medical professional, such as an urologist, who is manipulating the delivery system of the invention to deploy the implants described herein. Accordingly, those features of the delivery system held by the hand of the urologist are at the "proximal" end and the assembled system and the implant, initially in its compressed configuration, is located at the "distal" end of the delivery system.

Each of the embodiments of the invention described below is comprised of an implant having a plurality of tissue-engaging structures to exert a force against enlarged prostatic tissue proximate to the urethra. As described below, the number of the plurality of tissue-engaging structures can be 2, 4, or greater than 4 tissue-engaging extensions. The use of 3 extensions is avoided when the three extensions are oriented to each fit within the intralobular grooves of the prostate. Accordingly, any plurality of tissue engaging structures is a possibility as long as the structure is oriented asymmetrically to ensure that the implant is oriented outside the 3 intralobular grooves formed by the length of tissue contact between the 2 lateral and one medial lobes. Embodiments using three tissue-engaging structures may be used to treat anatomies when the urethral anatomy consists of bilateral lobes and the third lobe is not involved with urethral narrowing.

The implants of the invention may be fabricated from shape memory materials, alloys, spring materials, and super elastic materials including Nitinol (nickel-titanium alloy), Nitinol-based alloys, cobalt chromium alloys, spring steels, and spring stainless steels. Other known shape memory materials include poly-ether-ether-ketone (PEEK), and shape memory and bio-absorbable polymers and metals (polylactic acid, polyglycolic acid and their copolymers; magnesium alloys). The above materials may be coated with thin film coatings to prevent encrustation, corrosion and stone formation. Coatings may include ceramic materials like alumina, silicon carbide, silicon nitride and zirconia and other ceramic coatings that are inert to urine and prevent encrustation, stone formation and to prevent the deterioration of the material forming the implant in the chemical or urine environment. Coatings may also be polymers such as polytetrafluoroethylene (PTFE), Parylene, silver and other antimicrobial coatings, silicone derivatives, and other similar materials recognized by those of ordinary skill in the art.

The implant may also include therapeutic coatings adhered to the surface of the implant for controlled drug release following implantation in the prostatic urethra in the manner known for drug-eluting implants to reduce hyperplasia and tissue proliferation. The coatings contain pharmaceutically active anti-inflammatory drugs and anti-proliferative agents including sirolimus, novolimus, everolimus, biolimus, zotarolimus, paclitaxel and others that are used to prevent restenosis.

Implants of the invention may also be coated with drugs to treat BPH symptoms. Such embodiments have the advantage of using high locally high tissue closes in the diseased prostatic regions of the urethra for greater effectiveness to relax smooth muscle cells, reduce tissue proliferation and size of the prostate without incurring the side effects from drugs circulating in other parts of the body. Potential drug candidates include alpha-adrenergic blockers like, alfuzosin, doxazosin, tamsulosin, terazosin and silodosin. Other drug candidates include 5-alpha-reductase inhibitors like, dutasteride and finasteride, and anticholinergic agents. Other drug candidates are anti-cholinergic agents like, oxybutynin, fesoterodine, darifenacin, tolterodine tartrate, tolterodine, solifenacin. A combination of drugs may also be coated on the surface, including alpha blocker+5-alpha-reductase inhibitor or alpha blocker+anticholinergic agents. In addition, anti-infective agents or antimicrobial agents or antibiotics like fluoroquinolones (e.g., ciprofloxacin) macrolides, tetracyclines, and trimethoprim.

Typically, the drugs are mixed with solvents and polymers into solution and spray coated on the outer surface of the implant to achieve the desired drug release characteristics. The manufacturing processes are similar to those used for drug eluting stents used to treat coronary artery disease. Often, the coating may be on the abluminal side to ensure more effective drug release and deposition into the urethral tissue of the prostatic urethra and minimize washout during urine outflow. The drugs may also be deposited in micro-reservoirs or micro-depots on the outer surface of the implant to load the drug and covered by a polymeric coating to controllably elute drug into the urethral tissue. Typical polymers used to load the drugs are polylactic acid (PLA), poly-L-lactic acid (PLLA) polyglycolic acid (PGA), and their copolymers; polyurethanes; poly(methyl methacrylate) (PMMA) or poly(n-butyl methacrylate) (PBMA); and their combinations thereof. Other polymers and solvents may be used by those skilled in the art to load sufficient drug and maintain coating integrity with the implant surface. Multiple layers of coatings may be used to achieve the desired drug loading and controlled release characteristics.

Referring to FIG. 1, a cross-section of the male anatomy shows the prostate gland surrounding the urethra. The urethra, under normal conditions, provides fluid communication from urine stored in the bladder to be expelled from the body under voluntary muscular control of the external urethral sphincter. Normal or "true" prostate tissue surrounds the urethra and, in the absence of disease, does not impinge on the patency of the urethra. In patients suffering from benign prostatic hyperplasia (BPH), the urethra is narrowed by hyperplasic tissue, i.e. prostate tissue that exhibits excess growth towards the urethra. This excess of non-cancerous cellular growth leads to the symptoms of BPH described above, including, lower urinary tract symptoms (LUTS) and urinary outflow obstruction, and urinary incontinence. In FIG. 1, an embodiment of the implant 20 of the invention is shown engaging prostate tissue 5 along a length of the implant 20 to restore the patency of the urethra and to permit unimpeded urine flow from the bladder 1. The selective placement of the implant 20 at a target site, between bladder neck opening 2 and verumontanum 6, as shown is an important part of the invention because the implant 20 does not puncture or incise the surrounding tissue. The implant 20 is designed to remain in place within the urethra. The implant 20 does not extend into the urinary bladder 1, where the structural material of the implant 20 could become encrusted or otherwise degraded causing complications and making retrieval more difficult, and the implant 20 does not interfere with the voluntary control of the external urethral sphincter or interfere with sexual functions.

Referring to the FIGS. 2A-2B, an embodiment of an implant 20 of the invention is shown having linear arms as tissue-engaging elements 13a-13d extending substantially radially away from a terminal or proximal hub 11 such that each of the arms 12a-12d that form the tissue-engaging region have substantially the same length. Although the shape of the hub 11 is generally shown as annular in FIGS. 2-5, the hub may be formed of any shape that provides an attachment point for the arms 12a-12d as described below. Because the overall dimensions of the implant 20 adopt a different configuration as the device transforms from the compressed or constrained configuration to the expanded or unconstrained configuration, a region of the arms 12a-12d most proximate to the hub 11 may be described as a transitional region 15a-15d because this short portion of the arms 12a-12d transition from a substantially linear configuration, when the device is in the collapsed configuration to a curvilinear configuration when the implant 20 is in the expanded configuration or partially expanded configuration even if the length of the tissue engaging portions 13a-13d remains substantially linear as in FIG. 2A. Each of the transitional regions 15a-15d forms the connection between the hub 11 and the remainder of the arm 12a-12d comprised of the tissue engaging portions 13a-13d.

Referring to FIG. 2B, the structure of the hub 11 and its integrally formed features are shown in more detail. The hub 11 has a circumferential solid region 16 at the end thereof. A second portion of the hub 11 is circumferentially formed but may not be entirely solid about the circumference to allow recesses 18a, 18b to form the arms 12a-12d such that the hub 11 provides structural support for the implant device 20. The hub 11 may have an internal open space comprising a housing 17 that traverses the entirety of the body of the hub 11 or may be solid through at least the length of the hub from the most terminal and to the apex of the recesses 18a,18b at the point of attachment of the arms 12a-12d. As described in more detail below with respect to FIGS. 7 and 8, depending on the starting material construct from which the implant is fabricated, the hub may be a single unitary structure from which material is removed, or the individual structures such as the hub 11 and the arms 12a-12d can be fabricated separately and assembled into an integrally formed implant assembly. The hub element is integral to the implant and designed to incorporate three functional features. The hub provides a connection for the arms so that the arms exert a retraction or radial force on the prostatic lobes when deployed and implanted inside the urethra. Secondly, the hub and recesses allow the implant to be collapsed or constrained into a low-profile configuration inside the delivery system without exceeding the stress and strain limits of the material, thereby allowing the implant to recover to its unconstrained shape and dimensions after deployment. Thirdly, the shape of the hub is designed so that the implant can be introduced through the working port of the cystoscope in the constrained state and placed within the prostatic urethra. The implant may be pushed through the working or instrument channel of a cystoscope using a pushrod or push wire. Alternatively, the implant may be constrained inside a sheath of a delivery system, and the delivery system may be advanced through the working channel of a cystoscope.

Either by assembly, or by manufacturing from a single construct or material component, each tissue engaging region 13a-13d that is integrally connected with the hub 11 is comprised of at least a portion of the length of the arms 12a-12d and may be connected to the hub 11 by the transitional regions 15a-15d. Each individual arm 12a may be spaced away from each adjacent individual arm 12b at the point of the transitional region 15a by a small cutout portion 18a to facilitate expansion of the implant 20 from the compressed to the expanded configuration. As shown in FIG. 2A, each of the arms 12a-12d terminates at the end spaced farthest away from the hub 11 in an atraumatic end 14.

In the embodiment of FIG. 2A, the arms 12a-12d have substantially equal length and are oriented to deploy away from the hub 11 in the expanded configuration or unconstrained state or partially-constrained state in a substantially symmetrical manner. This design results in an overall orientation wherein the atraumatic ends 14 are positioned at an approximately equal distance from each other and at an equal distance the terminal hub 11 as shown. The tissue engaging portions 13a-13d of the arms 12a-12d preferably have a substantially flat or substantially planar ribbon-shape and, as a result of the manufacturing methodology described herein, can have equivalent or dissimilar widths or lengths or cross-sectional shapes and areas. Depending on the length of the arms 12a-12d and the configuration of the tissue-engaging regions 13a-13d, the implant may be symmetrical along an axis traversing the terminal hub 11, resulting in the hub 11 being centrally disposed in the urethra upon deployment, or may be designed for non-symmetric positioning of the hub 11 following deployment.

In another embodiment, the arms 12a-12d may be unequal in length in the deployed or undeployed state. The hub 11 may be oriented non-centrally so that it is positioned asymmetrically along the axis of the urethra where the terminal hub is oriented towards one side of the urethral wall. Such configurations have the advantage of limiting obstruction of the urethra after deployment. The atraumatic tips 14 reduce trauma to the urethral wall and may include rounded tips of the distal most end of the tissue engaging regions 13a-13d. Such a configuration is readily achieved by differentially heat-setting the implant 20 such that the atraumatic tips 14 of the arms 12a-12d are weaker than the remaining structure or by laser-cutting the tips to assume an atraumatic configuration. Heat setting may also be used to shape the atraumatic tips 14 such that the end portions are slightly curved inward (not shown) to minimize contact with the inner tissue layer of the urethral wall.

Typically, the implant 20 is made from hollow cylindrical tubes or hypotubes ranging in diameter between approximately 1-5 mm and wall thicknesses ranging between approximately 0.2-2 mm. More specifically, having outer diameters between approximately 1.5 and 3.0 mm and wall thickness ranging between approximately 0.2 mm and 1.2 mm. Typical width dimensions of the implant 20 are approximately 0.2-3.0 mm. More specifically, typical width dimensions of the arms are approximately 0.5-1.2 mm. The overall length of the implant 20 varies between approximately 10-100 mm. Implants are laser cut from small-diameter tubes in the collapsed or constrained configuration and shape-set to the desired dimensions. Alternatively, the implants may be fabricated from large diameter tubes in the expanded state, using tubes ranging between 5-50 mm in diameter, or more preferably 10-30 mm in diameter. They may then be collapsed to smaller size by crimping the implant to a smaller diameter and constraining them inside a sheath.

In other embodiments, the implant 20 may be laser-cut and polished from a solid tube to increase the force applied by the implant 20 on the prostatic tissue obstructing the urethra. The cross section of such implants is in the form of a quadrant of a circle, sextant of a circle or circular sector of a circle as described in FIGS. 7A-7D and 8A-8D. Such cross-sectional geometries provide the largest wall forces for a given surface area of the implant 20, and hence are highly desirable to reduce the incidence of encrustation, tissue growth and reduce the potential for migration of the implant. Typical diameters of the starting wire range between 1-5 mm and circular sector angles range between 20-180 degrees.

Typically, the total surface area of the implant is designed to vary between 10-100% of the total urethral surface area that is treated by the implant from one end to the other, or more preferably between 25-80%. The outer surface area of the implant in contact with the urethral wall is designed to vary between 5-50% of the total urethral surface area treated by the implant from one end to the other. The outer tissue-pushing or tissue engaging surface area, where the retraction forces are applied along the length of prostatic urethral lobes is designed to vary between 3-30% of the total urethral surface area treated by the implant from one end to the other. Such implant configurations provide the optimal retraction forces with minimal surface area to minimize or prevent encrustation and stone formation. In addition, the low surface area engaging and retracting the prostatic tissue and open the urethral lumen minimizes tissue growth over the implant and enables implant retrieval, when needed. Accordingly, the implant configurations described in this invention also provide high tissue retraction pressures or radial pressures, since the retraction forces are concentrated over small surface areas in contact with prostatic tissue, to open the narrowed lumen of the prostatic urethra while minimizing injury to the urethral surface. For one of the implants illustrated in FIG. 3B, the average retraction or radial force was measured to be 10N with a tissue-engaging outer contact surface area of 40 mm2, yielding a contact pressure of 0.25 N/mm2. Contact pressures for other embodiments described in this invention range between 0.1 to 4 N/mm2 depending on the features of the implant, including the number of arms, arm width, arm thickness, arm cross sectional shape and area, tissue engaging lengths, number of hubs. Similar calculations may be made for the retraction force or radial force per unit mass of the implant. Implant configurations described in this invention provide the most efficient us of mass to distribute the forces along the length of the prostatic urethra to open the lumen and provide LUTS relief.

Figure 2C:
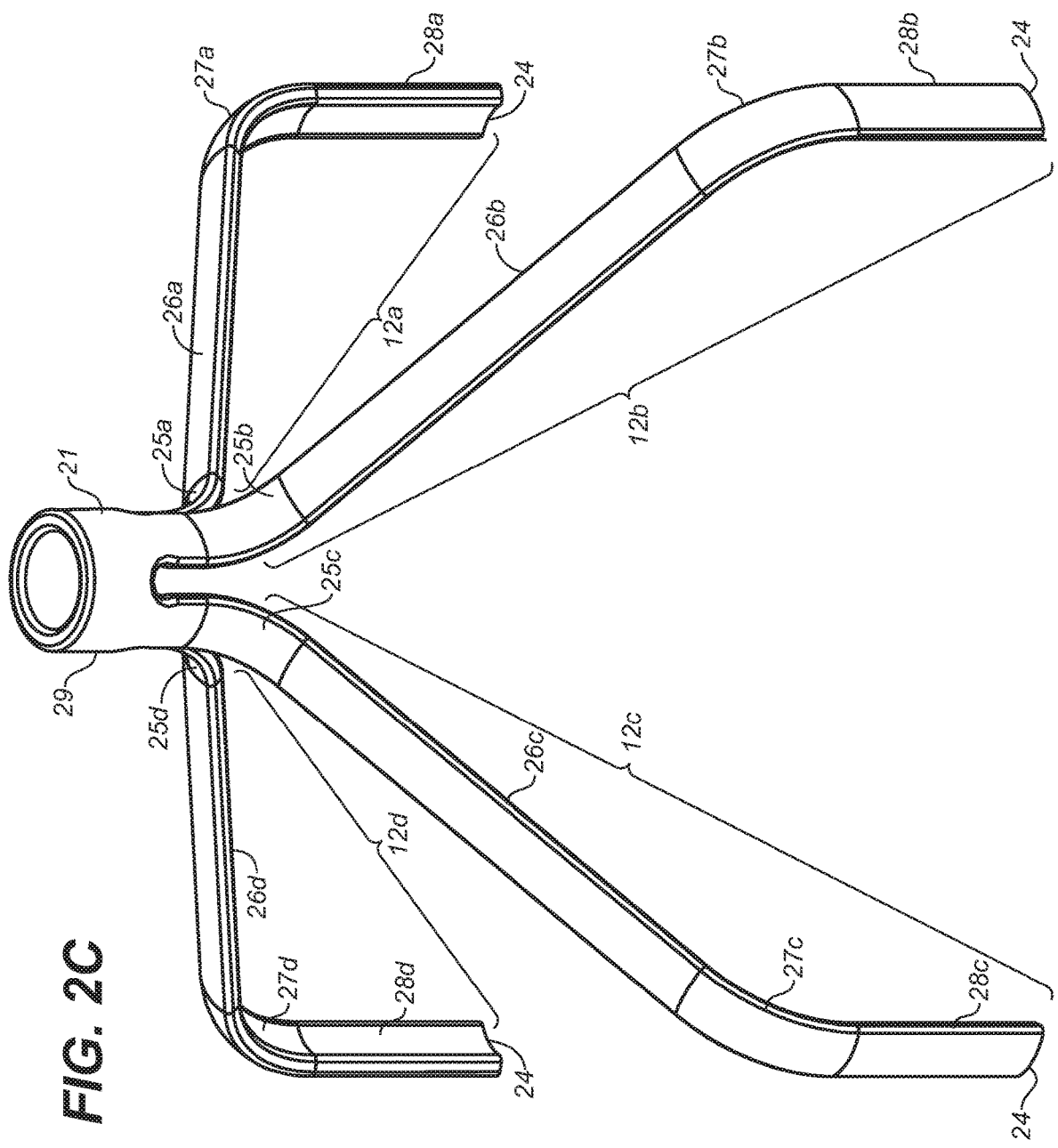
Figure 11A:
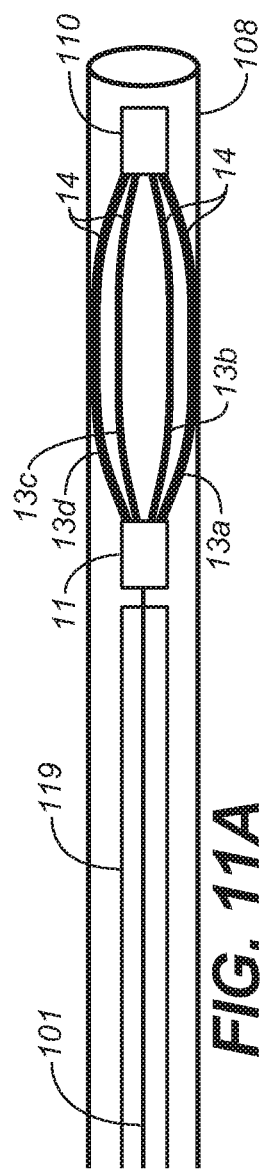
FIGS. 11A-C illustrate a progression of the deployment of an implant of the present invention using the delivery system of the invention at various stages of the placement of the implant and pursuant to a method of the present invention.
Figure 11B:
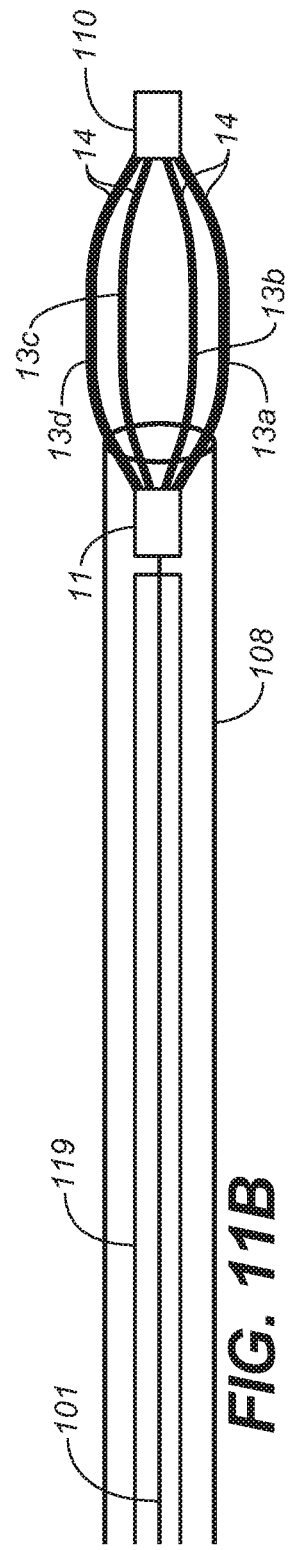
Figure 11C:
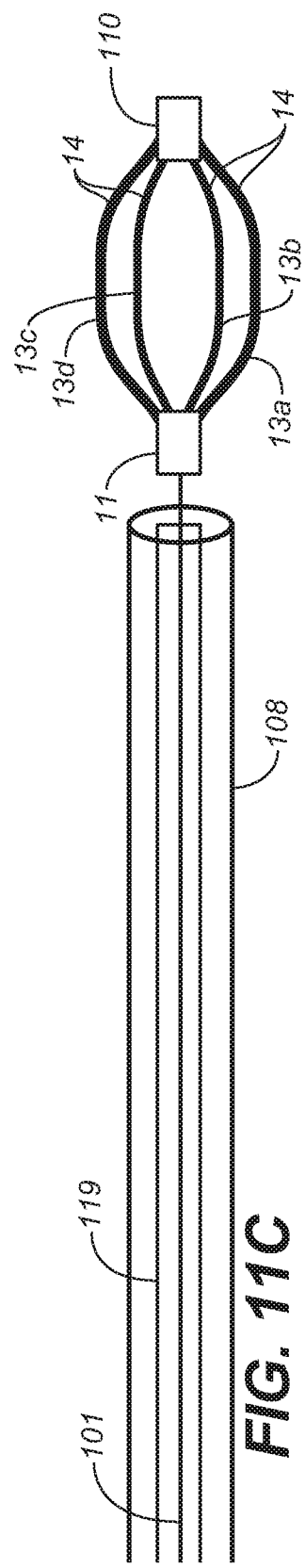

Referring to FIG. 2C, an embodiment of the implant 20 of the invention is shown with arms 12a-12d having a second curvilinear transitional regions 27a-27d along their length and a portion of the tissue engaging segments 28a-28d being substantially linear. The linear tissue engaging elements 28a-28d minimize trauma to the urethral wall from the tips 24 upon deployment and expansion in the urethra. The implant 20, has a hollow or solid terminal hub 21, and optionally an asymmetric notch 29 formed in the body of the hub 21. The asymmetric notch assists holding the implant during deployment, repositioning and retrieval of the implant using delivery systems and commercially available grasper devices used in urological procedures. As with the embodiment of FIG. 2A, the plurality of tissue-engaging regions 23a-23d extend radially away from the terminal hub 21 and are integrally connected with the terminal hub 21 by transitional regions 25a-25d, as in the embodiment of FIG. 2A. In the configuration of FIG. 2C, the transitional regions 25a-25d may be connected to intermediate sections 26a-26d disposed along the length of the arms 12a-12d and the transitional regions 25a-25d and tissue engaging regions 28a-28d. In the embodiment of FIG. 2C, each intermediate region 26a-26d transitions into a curve 27a-27d leading to a substantially linear tissue-engaging region 28a-28d. The length of the linear portion of the tissue-engaging region is preferably at least 1-10 mm including the range of 1-8 mm. The tissue-engaging portions 28a-28d each terminate in an atraumatic end 24. The general shape of each arm 12a-12d is comprised of the portion of the hub 21, the transitional regions 25a-25d, the intermediate regions 26a-26d, and the tissue engaging regions 28a-28d. As shown in FIGS. 11A-11C below, the implant 20 transforms from a compressed configuration or a constrained configuration inside a delivery system to an expanded configuration upon deployment. In the compressed configuration, the transitional regions 25a-25d, the intermediate regions 26a-26d, and the tissue engaging extensions 23a-23d are substantially co-linear and are constrained into a limited diameter within the delivery system (not shown). Upon deployment, the configuration of the implant 20 is restored to the overall dimensions of the expanded configuration or partially expanded or deployed configuration and assumes and orientation within the prostatic urethra as shown in FIG. 1.

Figure 3A:
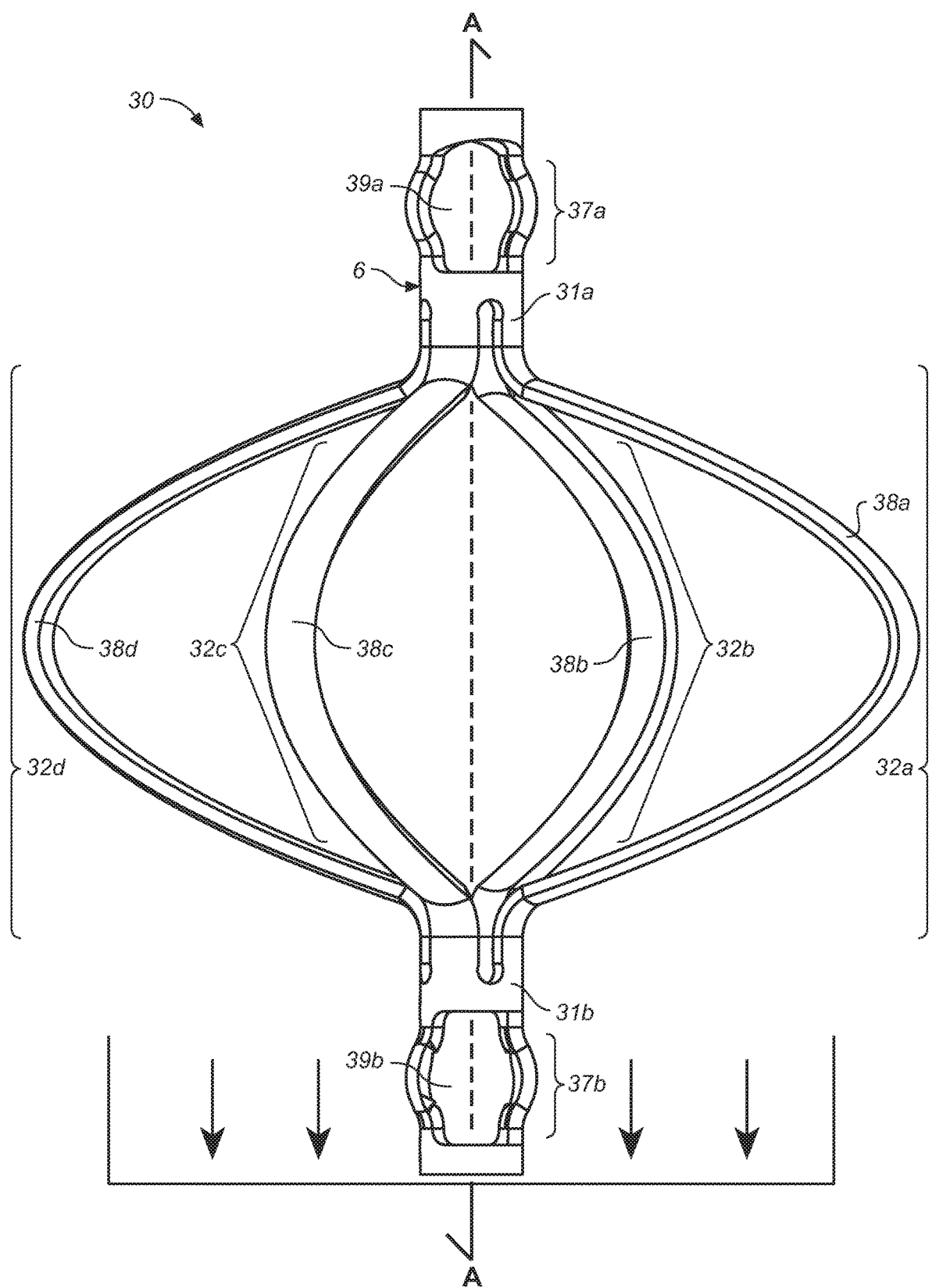
FIGS. 3A-3D are embodiments of the invention having both of a proximal and a distal hub at each end thereof and tissue-engaging arm regions extending away from and connecting each of the proximal and distal hub.

Referring to FIGS. 3A-3D, an embodiment of the implant 30 features tissue-engaging regions 38a-38d that do not terminate in an atraumatic end, but rather are formed of a continuous plurality of arms 32a-32d that terminate in attachment to a second terminal hub 31b. Referring to FIG. 3A, the two hubs may be described as a first proximal hub 31a and a second distal hub 32b having the plurality of arms 32a-32d extending between the hubs 31a and 31b to establish an integral connection therebetween. Furthermore, although these embodiments are shown with four arms, any plurality of arms numbering two or greater is within the scope of the invention. As described below, for embodiments having three arms, an orientation of the arms is preferred such that the overall orientation of the device does not result in the three arms being placed within the intra-lobular grooves of the prostate.

Accordingly, referring to FIG. 3A, in this embodiment of the invention the plurality of arms 38a-38d extend symmetrically away from and around a linear axis A-A such that an angle between each arm and the axis A-A is substantially equal and such that the angle of each arm 38a-38d relative to any adjacent arm is also substantially equal. The arms 38a-38d extend away from each hub 31a,31b in a similar fashion to the embodiment of FIGS. 2A-2B, except that the arms 38a-38d are continuous between the hubs 31a,31b and are each comprised of first and second transitional regions such as 35a,35a' and first and second intermediate regions 36a,36a', and centrally disposed tissue-engaging regions 38a-38d that are disposed formed between the hubs 31a, 31b.

Figure 3B:
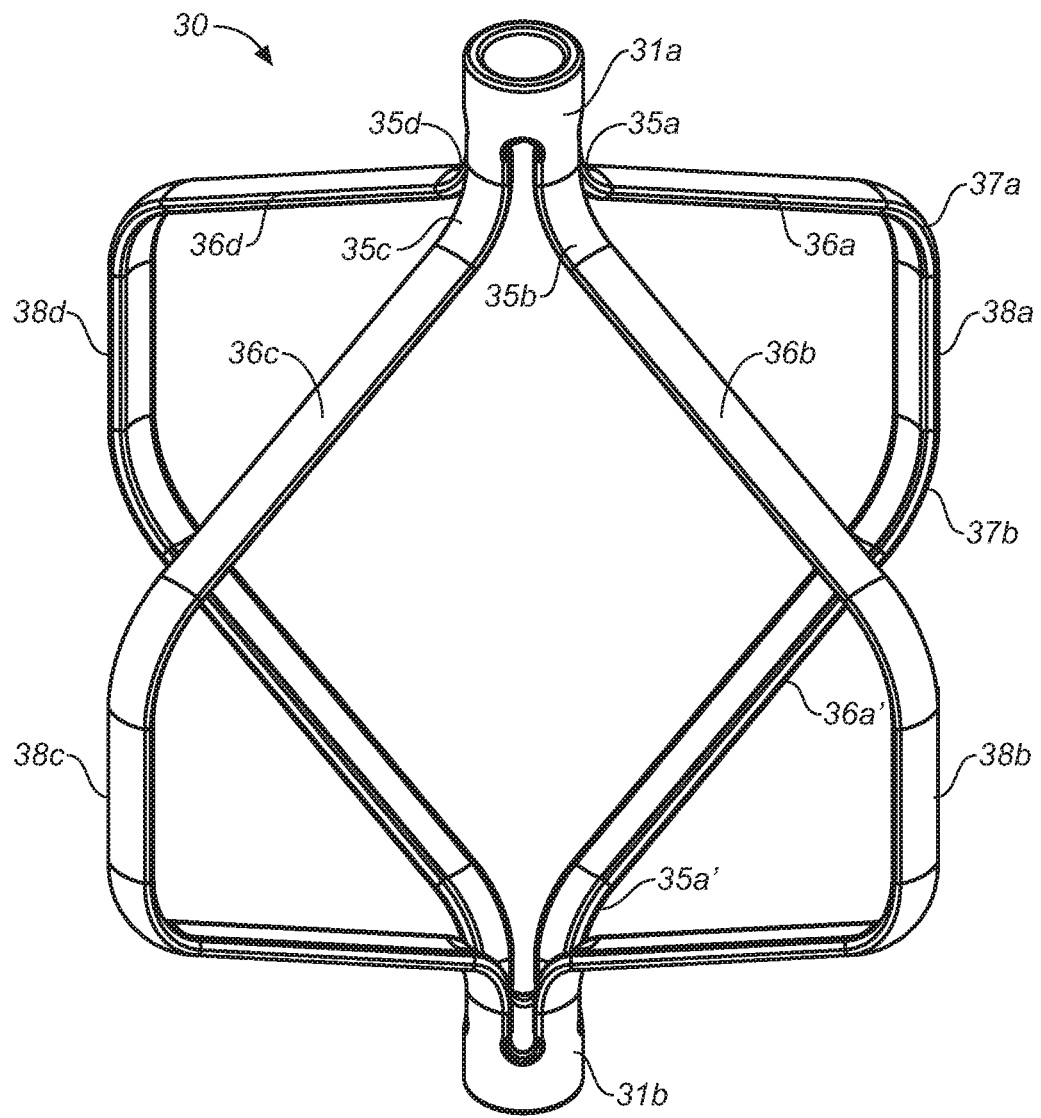
Figure 3C:
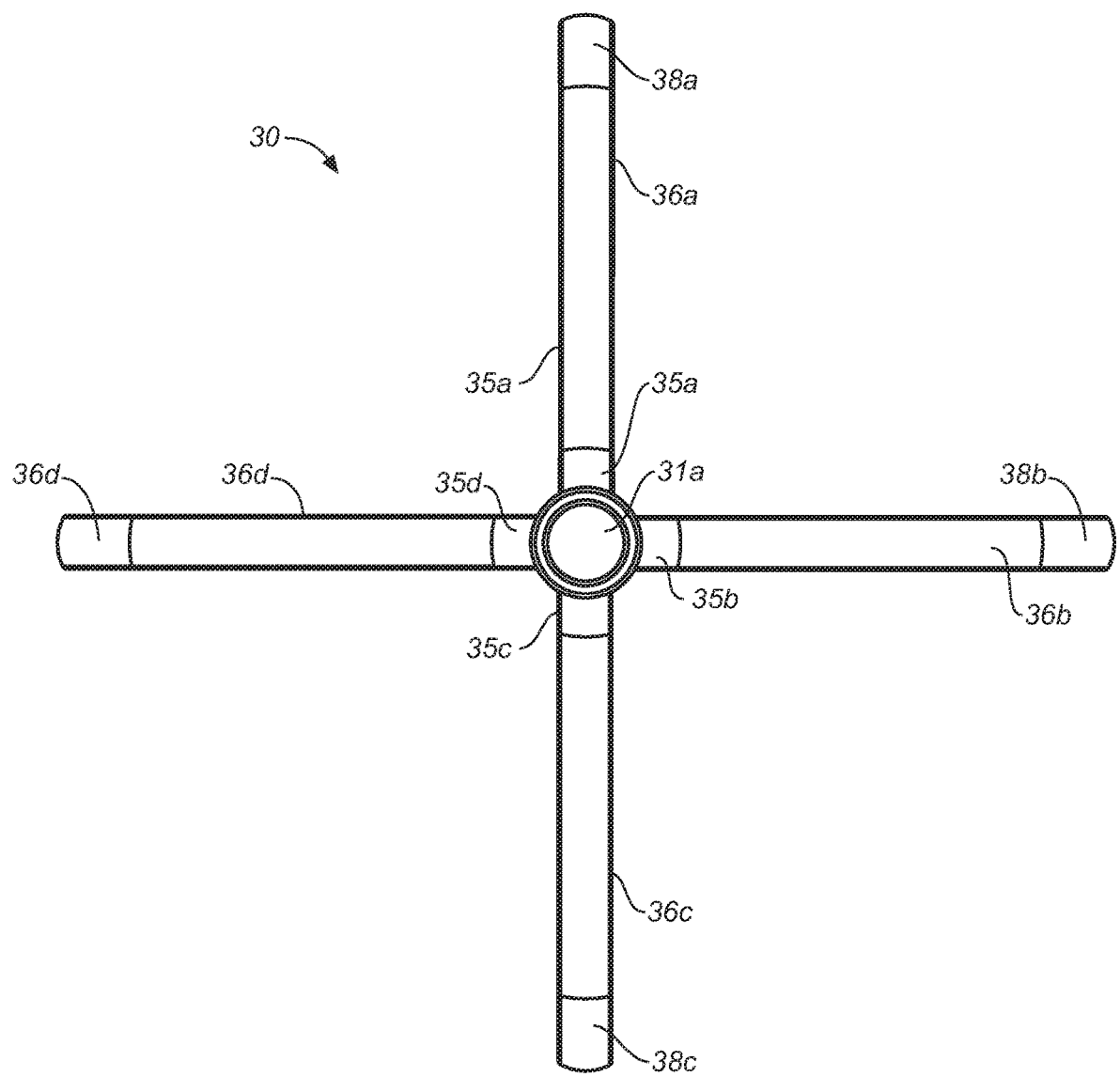
Figure 3D:
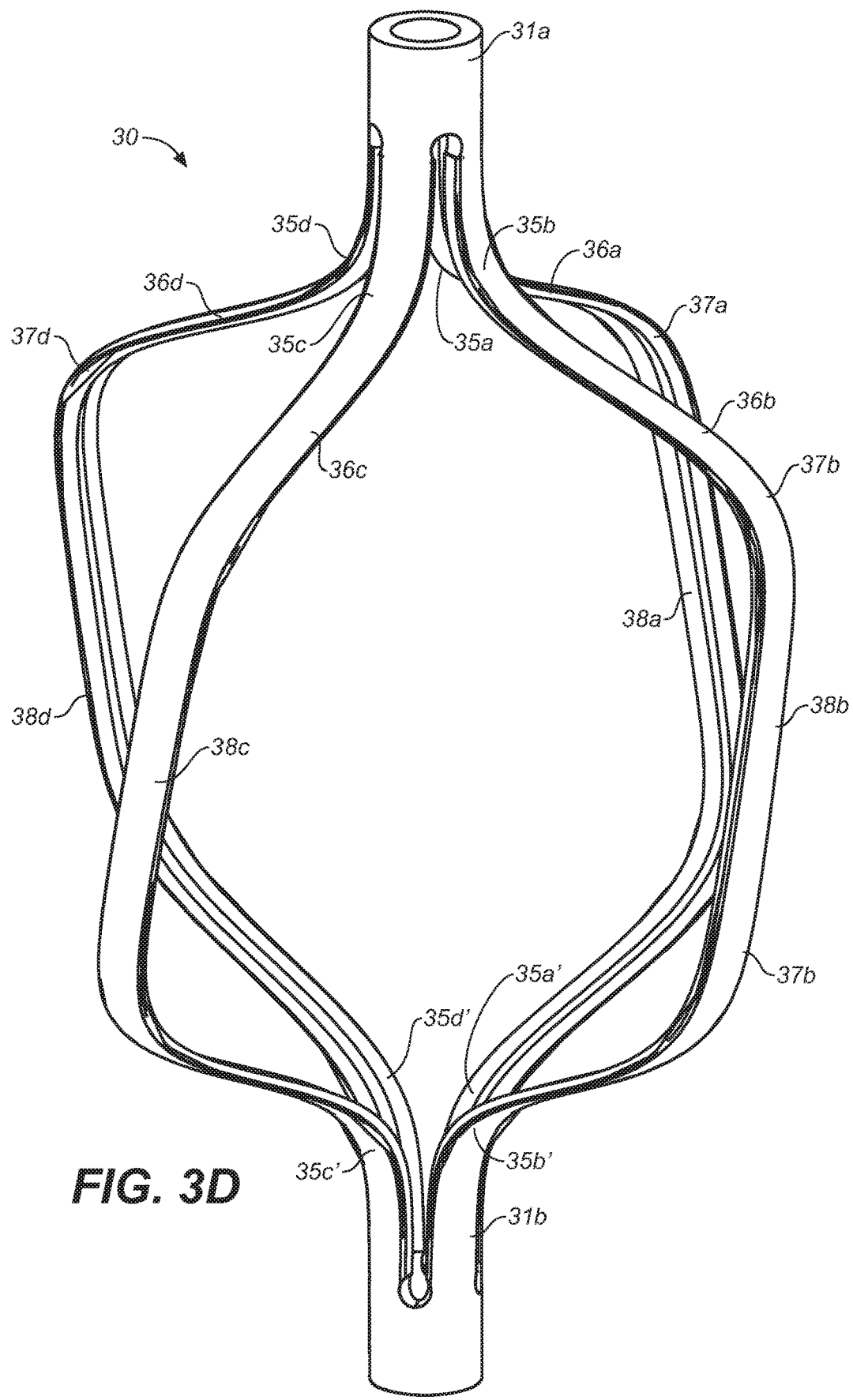

Referring to FIGS. 3B-3D, the tissue engaging regions 38a-38d may have a substantially linear portion having a length of at least 0.5 mm and with a range of 1 mm to 80 mm or more preferably between 1-20 mm. For purposes of definition, the distance of the linear tissue engaging regions 38a-38d are defined in the expanded configuration prior to engaging prostatic tissue and as defined by the shape-memory, elastic, superelastic mechanical properties or spring capabilities of the material from which the implant 30 is fabricated. As will be readily appreciated by one of skill in the art, after deployment within the urethra of a patient suffering from BPH, the overall dimensions of the implant 30 will partially conform to the surrounding tissue and so the dimensions after deployment may differ from those described herein.

Importantly, the linear distance separating the hubs 31a, 31b is a first distance when the implant 30 is in the collapsed configuration, such as when it is disposed in the distal end of the delivery system, as described below. Upon deployment into the expanded configuration, the hubs 31a, 31b assume a configuration where the linear distance separating the hubs 31a, 31b is a second distance wherein the second distance is less than the first distance. Typically, the ratio of the first distance to the second distance may range between 1-10, or more preferably may range between 1.2-3. Referring to FIG. 3D, while individual pairs of arms 38a-38d may the co-planar i.e., exist in a single plane, the hubs 31a,31b and the plurality of interconnected arms 38a-38d may assume a rotational orientation relative to each other so that the arms 38a-38d form a spiral configuration while maintaining the relative positioning of the transitional regions 35a-35d, the intermediate regions 36a-36d, and the tissue engaging regions 38a-38d.

Referring to again to the embodiments of FIGS. 3A-3D, the overall configuration and orientation of the implant 20 may be symmetrical about axis A-A as shown in FIG. 3A, particularly when each of the arms and specifically tissue-engaging regions 38a-38d are of equivalent dimensions. In such a configuration, the hubs 31a,31b are centrally disposed and are both traversed by axis A-A. As noted below, however, depending on the method of fabrication, the proximal and distal hubs 31a,31b may not be co-linear with a central axis A-A but may be displaced or offset from the central axis by purpose of design. The interior of the structure, specifically the area between the 2 terminal hubs 31a, 31b is hollow to facilitate the flow of urine around the implant 30 once the patency of the urethra is restored by the expansion of the tissue-engaging regions 38a-38d.

As with the embodiments of FIGS. 2A-2C, the embodiment of FIGS. 3A-3D, the tissue engaging regions 38a-38d are symmetrically oriented around the central axis A-A such that the hubs 31a,31b are centrally positioned. The length of the tissue engaging regions 38a-38d of the arms are parallel in the embodiments of FIGS. 3A-3D, such that enlarged prostate tissue is engaged along the linear portion of their arms at substantially equivalent points relative to the central axis. In other embodiments, the arms may be oriented asymmetrically around the central axis and have asymmetric shapes. In addition the hubs may be offset on either ends so that they are not located centrally and are positioned closed to a first urethral surface on one end and a second diametrically-opposite (180 degrees) urethral surface on the other end.

The outer surface of each tissue-engaging regions in any of the implants shown herein may be further comprised of structures or features that function to prevent slippage or movement of the implant along the urethra, into the urinary bladder or exit through the penis, once the implant is deployed. These structural elements may be any of barbs, hooks, surface texturing, or any mechanical expedient that engages tissue along the length of the outer surface of the implant along the points of contact with the interior lumen of the urethra. This embodiment further prevents the tissue-contacting regions from positioning the implant or expander completely within the grooves of the intra-prostatic lobes.

As noted above, the implant or expander device described herein is retrievable following deployment in the prostate and implantation for a given period of time as recommended by the urologist. The implantation period in the prostatic urethra may range from 30 days to a few years. To facilitate retrieval of the implant or expander at the desired time, it may be constructed to have an integral retrieval fixture 37a,37b, as shown in FIG. 3A affixed to the terminal end of the hub. The fixture 37a,37b may have an opening 39a,39b that are engaged by a retriever or any commercially retrieval or grasper device, such as the distal end of a catheter wire during the retrieval process as described below. One retrieval fixture may be affixed on one terminal end of the hub or two fixtures may be designed on both hubs of the implant. In other embodiments, the fixtures 37a and 37b may be simple hooks in the shape of a U to be engaged by a snare device to engage the implant for retrieval into a sheath. Other fixtures for retrieval may be designed on one or both ends by those skilled in the art to retrieve the implant.

In another embodiment of the device, it may be constructed using a single hub 31b on one end, as shown in FIG. 3B, connected by four arms and two hubs 31a1 and 31a2 (not shown), constructed by splitting hub 31a into two parts 31a1 and 31a2 (not shown). Each of the hubs 31a1 and 31a2 are connected by two arms. Such a construct may be deployed in the prostatic urethra with the hubs 31a1 and 31a2 oriented towards the bladder neck and the hub 31b oriented towards the external sphincter. Such a configuration minimized the obstruction of the urethra and facilitates passage and placement of a Foley urinary catheter or imaging cystoscope, when needed. A number of different combinations may be used, by those skilled in the art, to make different implants with one or more hubs on one or both ends, with the hubs connecting at least two or more arms to enable the implant to have sufficient expansion force to retract the hyperplastic prostatic tissue and open the lumen of the urethra.

Figure 4:
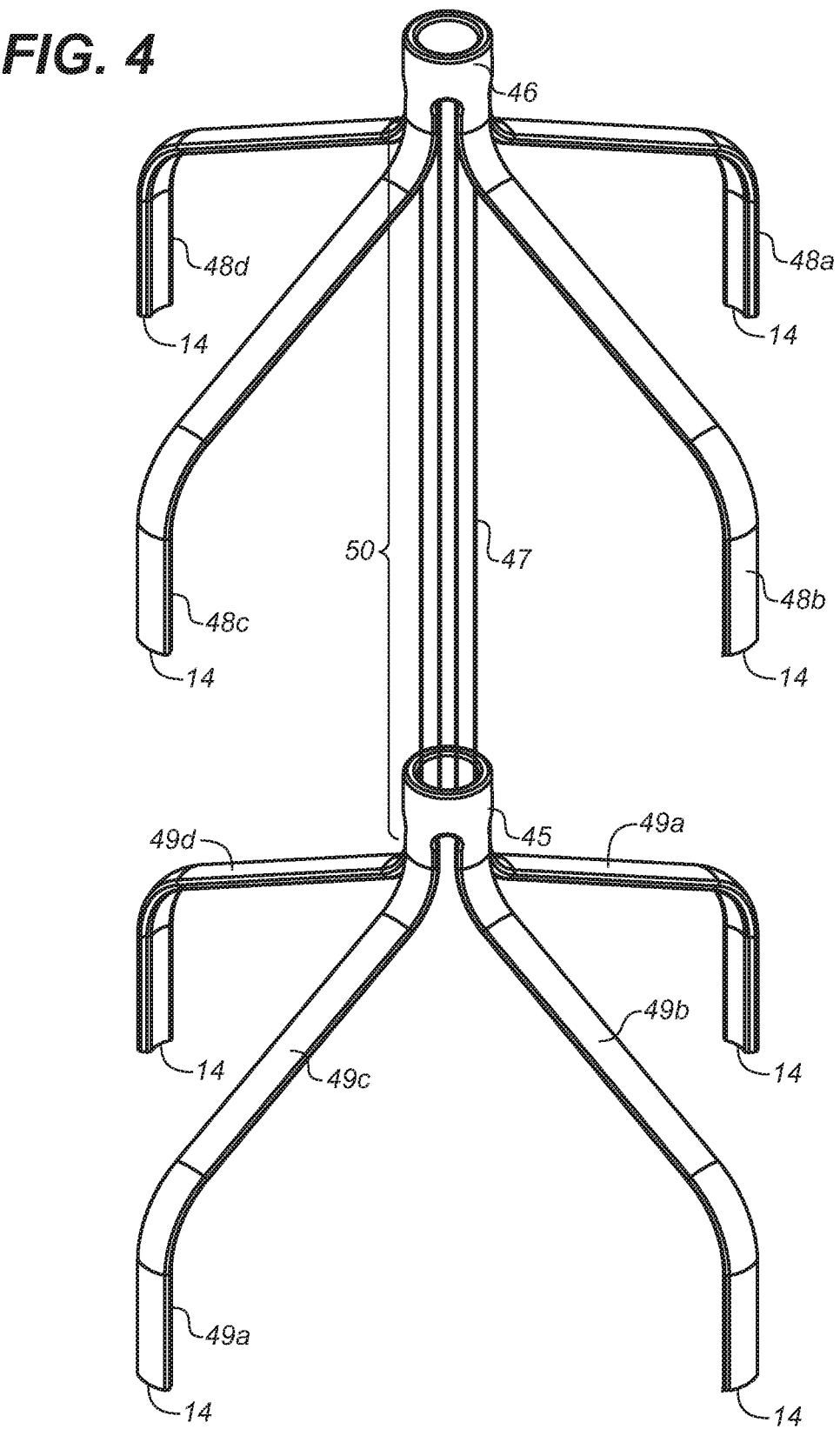
FIG. 4 is an alternate embodiment of the invention illustrated in FIG. 2 having a pair of hubs, where one hub is that a terminal and (either proximal or distal) and the second hub is at an intermediate point of the overall length of the device. The tissue engaging regions extend in the same direction and the inferior portion of the terminal hub is connected to the superior portion of the second intermediate hub by a shaft therebetween.

Referring to FIG. 4, in addition to placing multiple individual implants separately within the urethra to retract prostatic tissue along a greater distance than is possible with the single implant (to treat a long prostatic urethra), the implant of the invention can be provided in a double-aligned configuration that retracts tissue along an axial length of the urethra defined by the length of the pairs of the plurality of tissue-engaging regions. In the embodiment of FIG. 4, a pair of implants of the design of FIGS. 2A-2B are joined at and intermediate hub 45 to create a joining intermediate axis connecting member 47 from which the 2 sets of tissue-engaging members 43a-43d, 49a-49d extend. Proximal tissue engaging regions 48a-48d and distal tissue engaging regions 49a-49d extend symmetrically away from the intermediate axis 42 and open the urethral obstruction in the prostatic urethra. As in the embodiment of FIG. 2B, the arms have a sigmoid curve shape and extend to tissue-engaging regions having a linear portion 43a-43d and that each terminate in an atraumatic tip 14. One or more intermediate hubs may be used to construct implants of longer length to treat longer urethras.

The embodiment in FIG. 4 may be fabricated as a single integral structure without the need for joining at the intermediate hub 47. It may be made from a hypotube of a nickel-titanium (superelastic or shape memory nitinol) material using laser cutting, cleaning, shape setting and electropolishing processes, known to those skilled in the art. In addition, the intermediate hub 45 may be a hollow tube or a solid tube.

In other embodiments the intermediate axis or hub connecting member 47 may incorporate features that make the implant less rigid and conform to the anatomy. For example, the connecting member 50 may consist of one or more straight, angled, slanted, sinusoidal, spiral, or curved connector elements 47 that provide structure and flexibility to the implant and can be comprised of a shaft having one or more elongated connecting members of substantially circular, rectangular or square cross-section.

Figure 5:
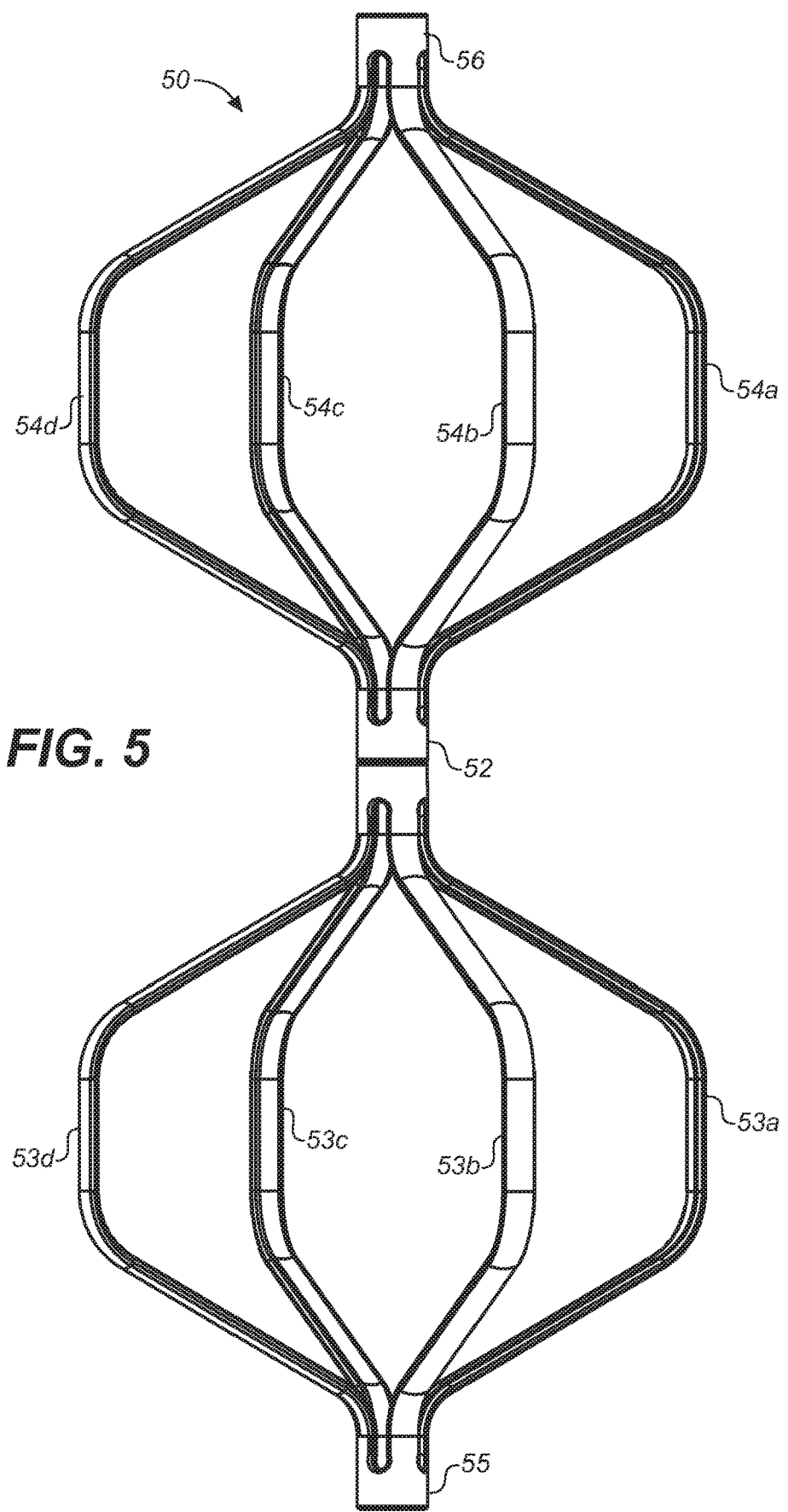
FIG. 5 is a double embodiment of the design of FIGS. 3A-3D having two sets of tissue-engaging arms interconnected between either of a proximal hub or a distal hub and an intermediate portion.

Referring to FIG. 5, a double-ended configuration of the embodiment of FIGS. 3A-3E achieves the same advantages of the embodiment of FIG. 4 with the ability to treat a long urethra with a narrowed lumen due to BPH. An intermediate hub 52 joins 2 sets of tissue engaging regions 53a-53d, 54a-54d having a linear portions 44a-44d and having a minimum length of 1 mm, between 3 mm and 5 mm, between 5 mm and 10 mm in all integral values therein respectively. As in the embodiment of FIG. 4, the implant has two separate tissue-engaging regions with similar or pre-selected and different diameters and has both a proximal hub 55, and a distal hub 56 for atraumatic insertion and delivery to retract prostatic tissue at two selected regions and similarly atraumatic retrieval by any of the methods as described herein for the other embodiments.

As described above, one or more intermediate hubs 52 may be used to construct implants of different lengths. In addition, the expanded diameters of the proximal arms may be different from the expanded diameters of the distal arms although the constrained diameter of the implant in the delivery system is the same along the length of the implant. The embodiment in FIG. 5 may be made as unitary structure without the need for joining at the intermediate hub 52 as described above by laser cutting the desired pattern from a nitinol hypotube and shape setting to the desired dimensions. Additionally, each of the structural elements on the implant (hubs, arms, transitional regions, diameters, lengths, retrieval fixture) may be a combination of symmetrical and asymmetrical features to optimize the implant to facilitate retraction of the prostatic tissue upon deployment in the urethra and facilitate retrieval of the implant, when desired.

Figure 6A:
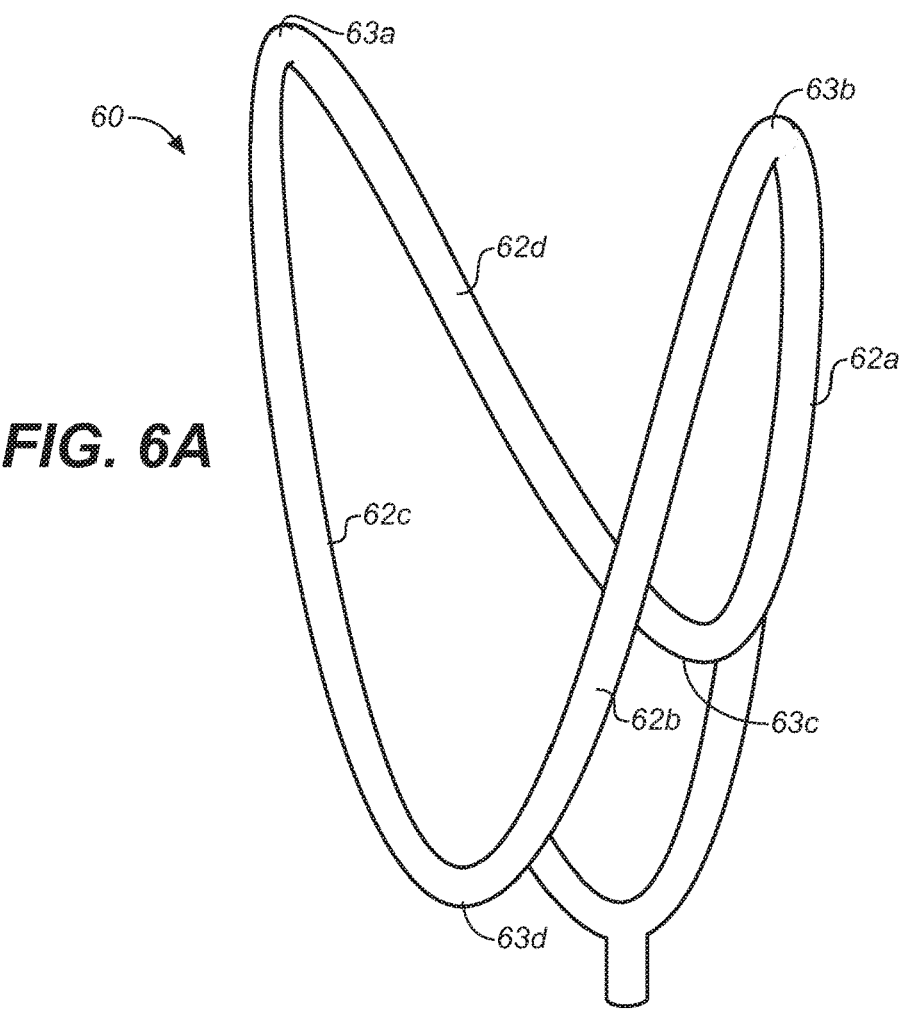
FIGS. 6A-6F are embodiments of the present invention wherein the entire implant is formed from a continuous or unitary wire, ribbon, sheet or tube structure. The embodiments of FIGS. 6B-6F have tissue-engaging regions with a substantially linear segment formed along a length thereof and connected by arcs at opposing ends of the implant. The embodiment of 6A shows an additional retrieval element connecting regions near 63c and 63d to facilitate grasping and removal of the device, when necessary.

Referring to FIG. 6A-6F, an embodiment of the implant 60 of the invention is formed from a continuous wire, ribbon or tube. The continuous wire implant 60, as shown in FIG. 6A, is in an expanded condition and features tissue engaging regions 62a-d formed upon expansion of the continuous wire implant 60 following deployment. When constrained within the outer sheath 108 (see FIGS. 11 and 12A) during delivery and deployment, the continuous wire implant 60 is tightly compressed within the inner diameter of the outer sheath 108 and in this configuration the implant 60 has four sharp turns 63a-d, that revert to form a series of curves 63a-63d in the expanded configuration, to retract prostatic tissue along the length of the tissue engaging regions 62a-d. The curves 63a-d act as interconnecting segments for the tissue engaging regions 62a-d. The arc of the four curves 63a-d is predetermined such that the implant 60 assumes a predetermined shape in accord with the shape memory properties of the material from which the implant 60 is fabricated. The length of the tissue engaging regions 62a-d have an individual length generally consistent with the retrievable implants of FIGS. 2-5, and as described above with the ability to treat urethra of sufficient length, by engaging and exerting direct radial forces on lobes of the prostate. The embodiment of 6A shows an additional retrieval element connecting regions near 63c and 63d, to facilitate grasping and removal of the device, when necessary.

Figure 6B:
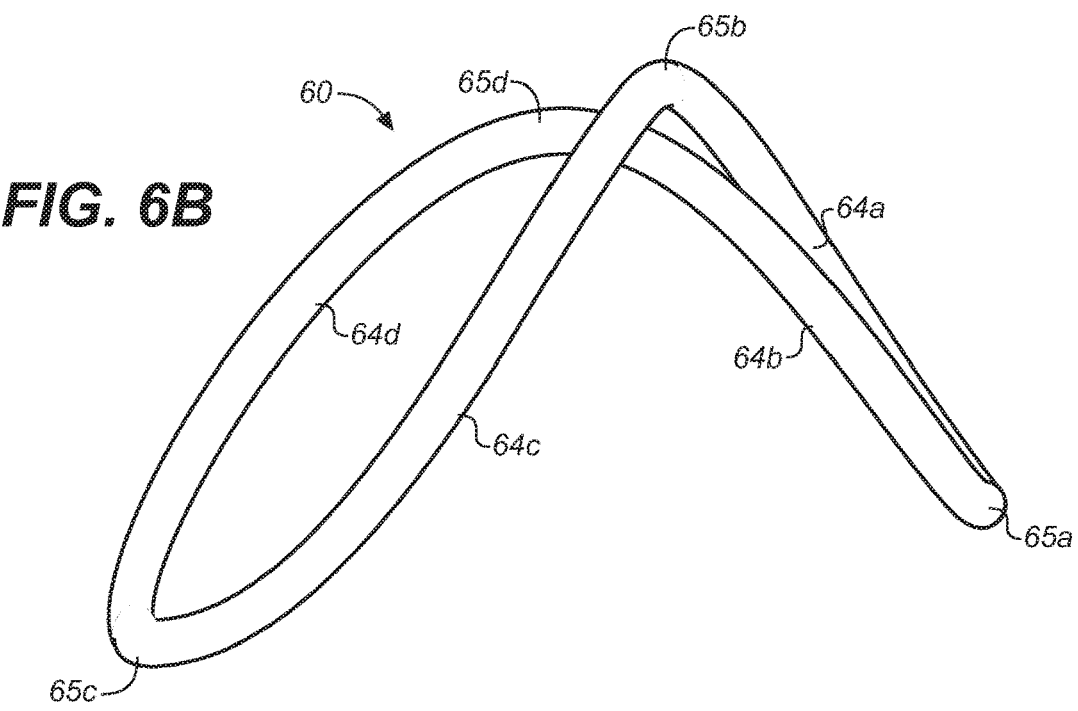

FIG. 6B is an alternative embodiment of the continuous wire or ribbon implant 60 in the expanded configuration having tissue engaging regions formed by the intersection of a first tissue engaging region 64a, a second tissue engaging region 64c, a third tissue engaging region 64c and a fourth tissue-engaging region 64d. In the unexpanded or constrained state inside a delivery system, the tissue-engaging regions 64a-d are substantially linear along an axis defined by the lumen of the delivery catheter. Upon deployment inside the urethra, the implant 60 takes the shape shown in FIG. 6B, in a three-dimensional U-shape configuration, with a first pair of tissue engaging regions 64a,64b engaging one side of enlarged tissue in the prostate lumen and a second pair of tissue engaging regions 64c,64d engaging an opposite side of the enlarged tissue to apply retraction forces on the urethral wall of the prostate. As in the embodiment of FIG. 6A, in the collapsed configuration the implant 60 has four sharp turns 65a-d in the confined configuration that transform, by the shape memory or superelastic or spring properties of the material from which the implant 60 is formed, into smooth curves upon expansion. The embodiment of FIG. 6B is formed such that tissue engaging regions 64a and 64b extend at one end of the implant extend away from the turns 65c at the other end of the implant by the close engagement of intermediate terms 65b, 65d that are centrally disposed along the length of the implant 60.

Figure 6C:
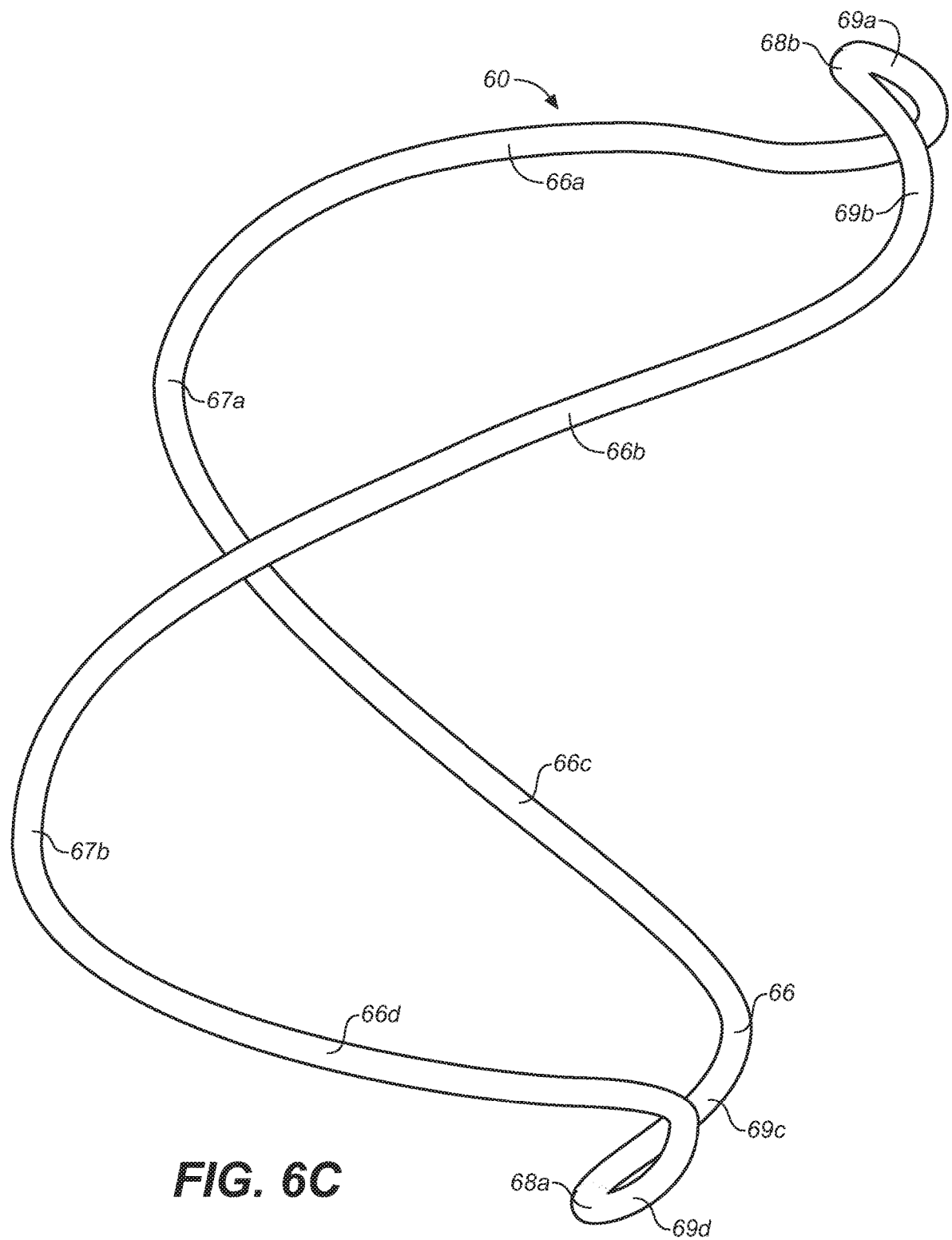

FIG. 6C is an alternative embodiment of the continuous wire or ribbon implant 60 in the expanded configuration having tissue engaging regions 66a-66d that are atraumatic. The additional turns 68a-68b form additional tissue engaging regions 69a-69d. It will be appreciated by one of skill in the art that the configurations that utilize the continuous wire embodiment are less dependent on precise placement within the prostatic urethra and do to varying orientations upon deployment, and due to differing regions in the physiology of any individual patient, the tissue-engaging portions 66a-66d, 69a-69d may be a subset of all of the regions defined as tissue-engaging portions. The implant 60 configuration is modified to engage more prostatic tissue and reduce the stress concentration by forming a small loop at the end that forms tissue-engaging regions 69a-69d. As described above, the tissue-engaging regions 66a-66d, 69a-69d are substantially linear along an axis in the constrained or unexpanded state inside the delivery system. Upon deployment inside the urethra, the implant 60 takes the shape shown in FIG. 6C, in a three-dimensional saddle-like or W-shaped shape configuration.

Figure 6D:
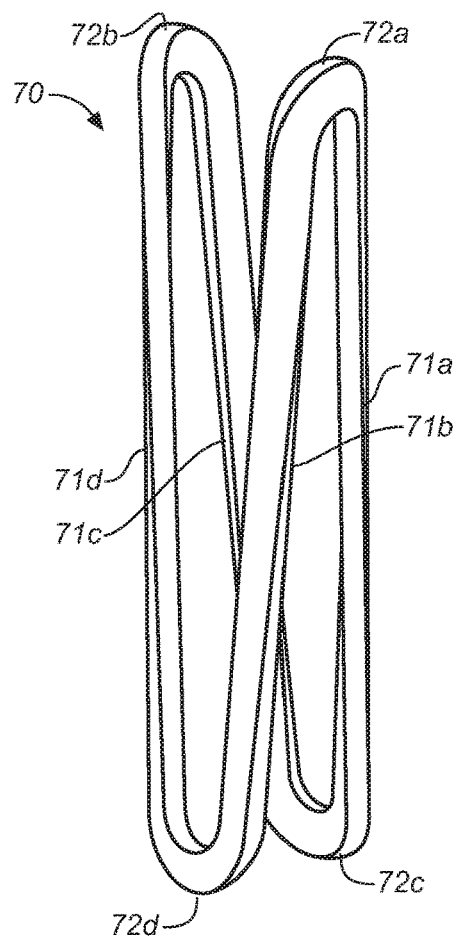
Figure 6F:
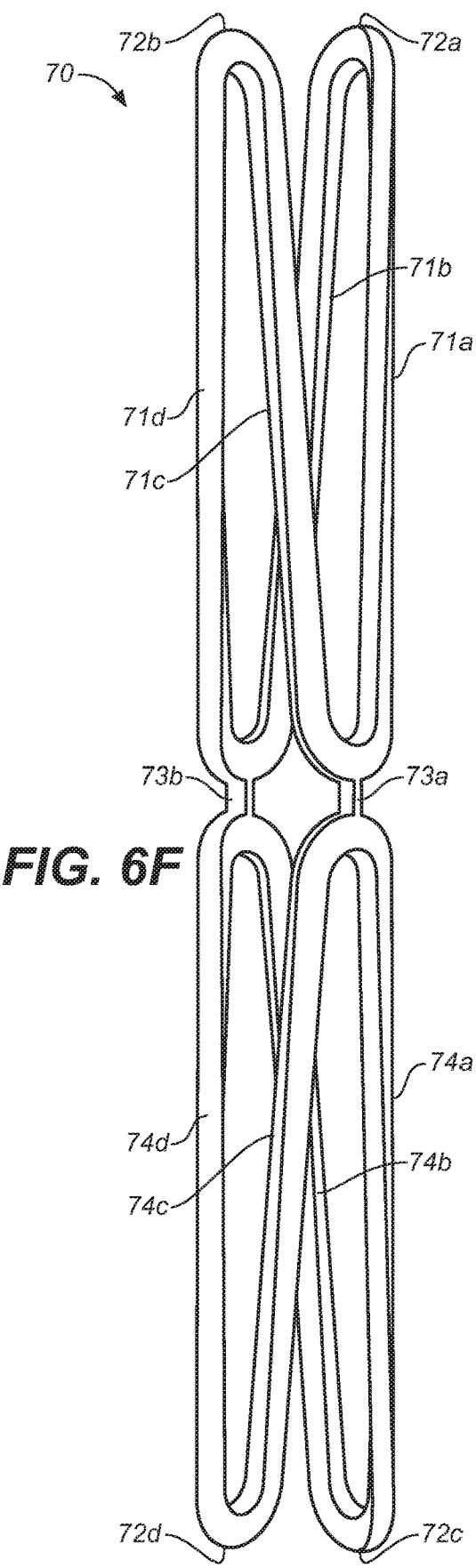
Figure 6E:
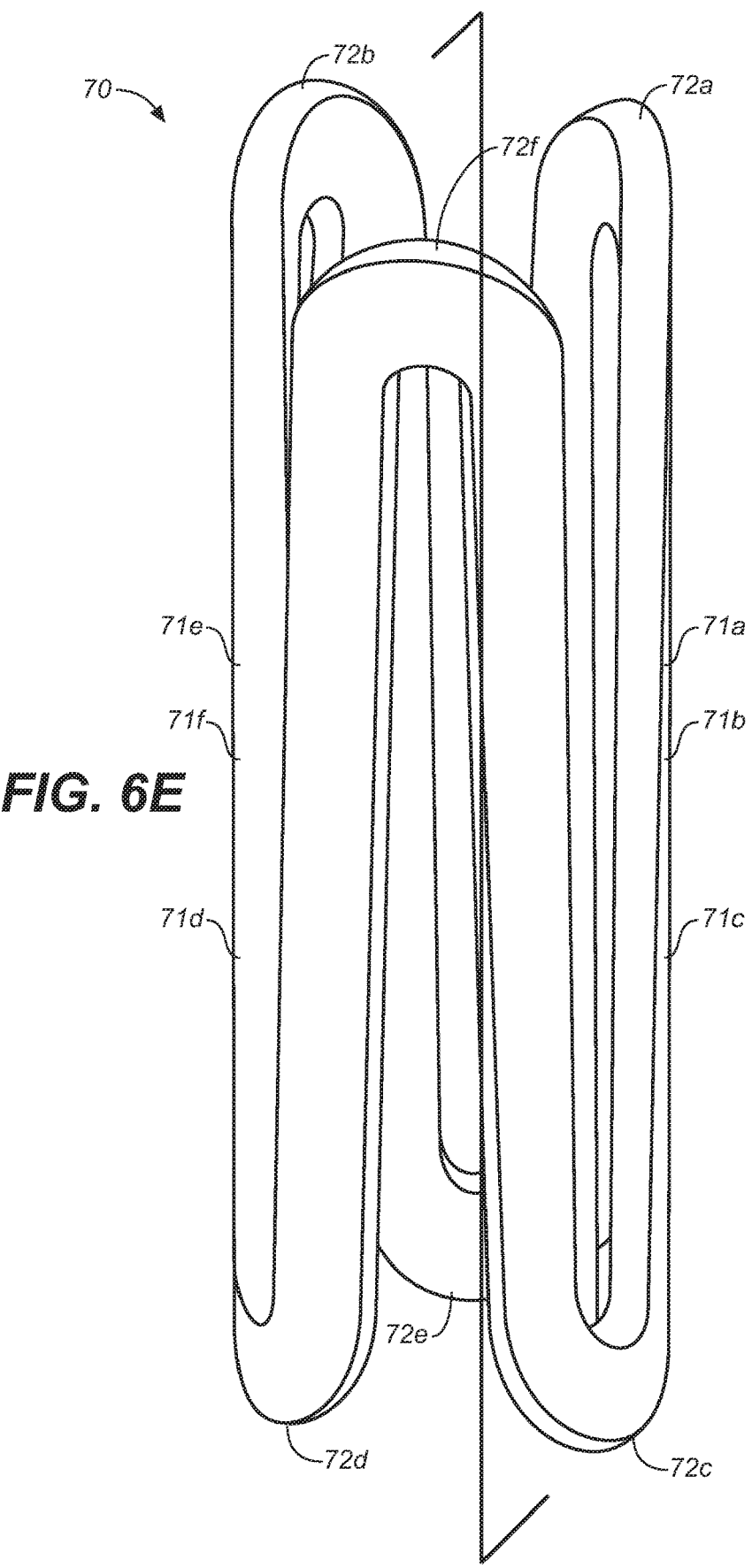

FIG. 6D and FIG. 6E are continuous wire embodiments of FIGS. 6A and 6B, having a sine wave form and configured to have arched proximal and distal end regions. A retrieval feature, as shown in FIG. 6A, may additionally be incorporated to facilitate repositioning of the implant during deployment or removal of the implant after a given implantation period, as desired.

Referring to FIG. 6E-6F, an embodiment of the implant 70 of the invention is formed from a continuous wire having a sine wave form and configured to have arched proximal and distal end regions. In this embodiment, the tissue engaging regions 71a-d are formed by a substantially straight length of the continuous wire. The proximal and distal ends of the continuous wire are comprised of the arched end regions 72a, 72b, and 72c, 72d, respectively. The embodiment of FIG. 6E has the same shape and configuration as FIG. 6D but is comprised of six tissue engaging regions 71a-f and having three arched end regions at each of the proximal and distal ends 72a, 72c, 72e, and 72b, 72d, 72f, respectively. The material from which the implant 70 is constructed is characterized as a flat wire or "ribbon" width of the surface facing both the prostatic tissue and the interior space of the implant 70 has a width that is equal to or greater than its depth. Preferable dimensions include, but are not limited to, a thickness in the range of 0.0055-0.055 inches, and more preferably approximately between 0.011-0.025 inches and a width range of between 0.01-0.18 inches with a preferable width range of approximately between 0.02-0.14 inches. These devices are placed such that the axis A-A traverses the length of the urethra, although the designation of the proximal or distal end is arbitrary, an orientation such that the proximal and distal ends respectively, are located along the linear path of the urethra is necessary.

The embodiment of FIG. 6F is a stacked or paired configuration of the embodiment of FIG. 6D, having eight total tissue engaging regions 71a-d, 74a-d and which are joined by interconnecting links 73a, 73b. The proximal and distal ends are formed by the most distal pair of arched regions 72a,b, most proximal end is formed by a most proximal pair of arched regions 72c,d, although as noted above, the distinction is arbitrary because this embodiment is symmetrical across a horizontal axis of the device.

Figure 7A:
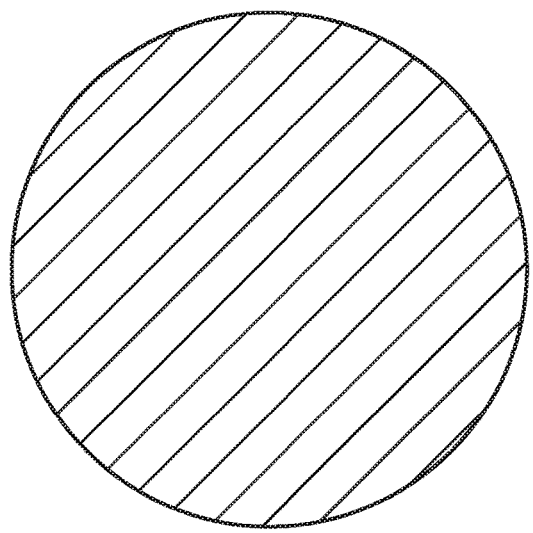
FIG. 7A-7D are starting materials for the fabrication of different embodiments of the invention wherein material is selectively removed from a length of the construct at a traversing radial distance of the body of the construct and wherein the material is removed from the construct along a length that is circular in cross-section.
Figure 7B:
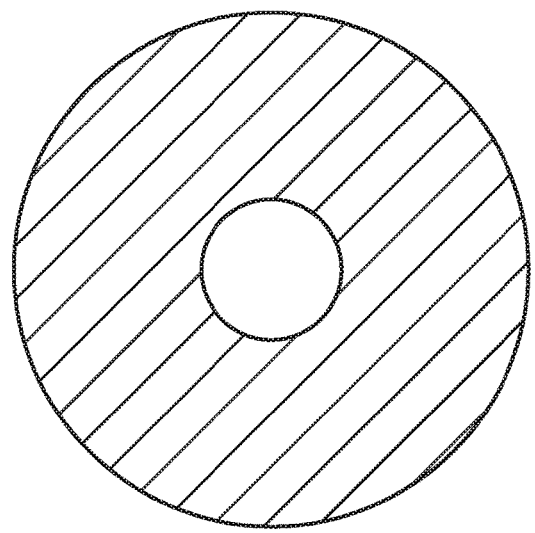
Figure 7C:
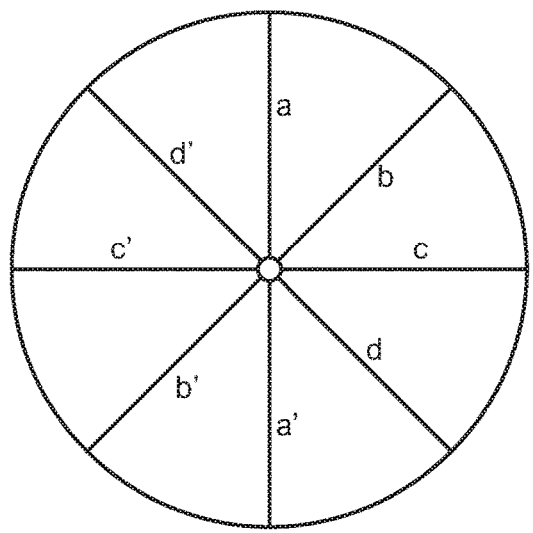
Figure 7D:
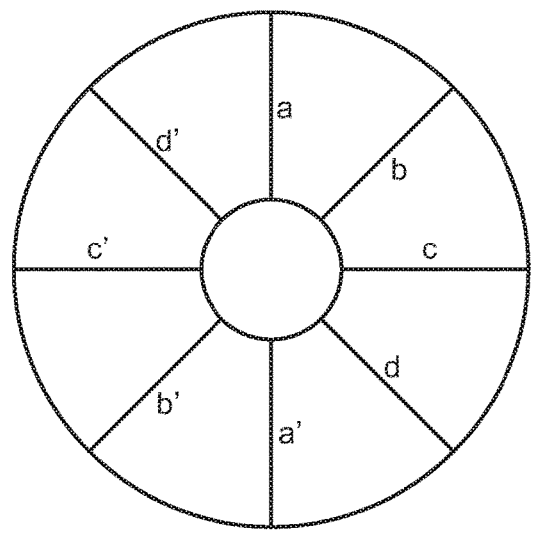

FIGS. 7A-7D illustrate the starting materials and fabrication processes for any of the embodiments of FIGS. 2-6. The starting material may be a solid tube or wire, as shown in FIGS. 7A and 7C, or may be a hollow tube, as shown in FIGS. 7B and 7D. Fabrication of different embodiments of the invention selectively removes material along the length of a construct by traversing a radial distance from the outer surface of the body of the construct. The radial distance may traverse the entire diameter or thickness of the tube or only a partially towards the center of the circular wire or tube. Selective or removal of material along the length of the construct creates the individual arms of the implant. The pattern from which material is removed from the construct dictates the shape, cross section, number and orientation of the arms. Removing material from less than the entire linear dimension along the length of the construct retains the integrity of the terminal hub without the need for joining. In the case of a single terminal hub, such as in the embodiment of FIGS. 2A-2B, material is removed from an intermediate point proximate to a single terminal hub and along the entire length of the remainder of the construct. By retaining a terminal hub at both ends of the construct, the embodiment of FIGS. 3A-3B is manufactured wherein the material is removed selectively from the construct along a length of the wire or tube in a given pattern to form the desired implant shape and dimensions. Laser cutting or electrodischarge machining (EDM), shape setting and electropolishing are commonly used manufacturing processes used to fabricate the implant.

Figure 8A:
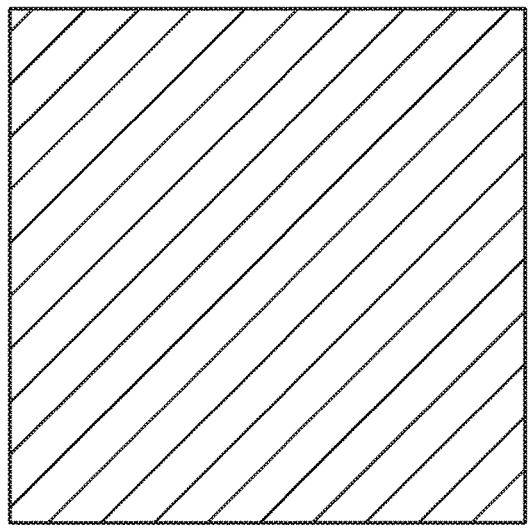
FIG. 8A-8D are starting materials for the fabrication of different embodiments of the invention wherein material is selectively removed from a length of the construct at a traversing radial distance of the body of the construct and wherein the material is removed from the construct along a length that is rectangular in cross-section.
Figure 8B:
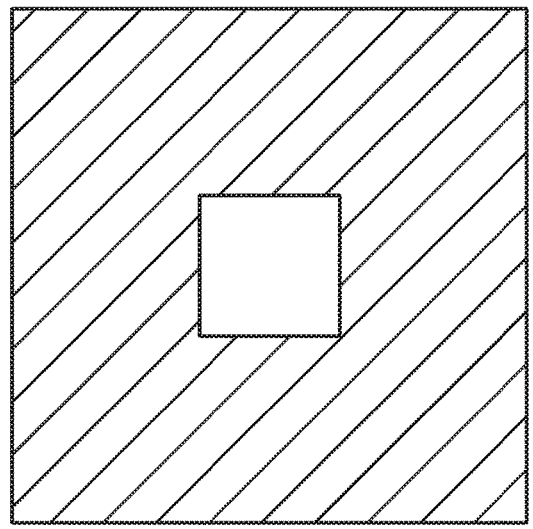
Figure 8C:
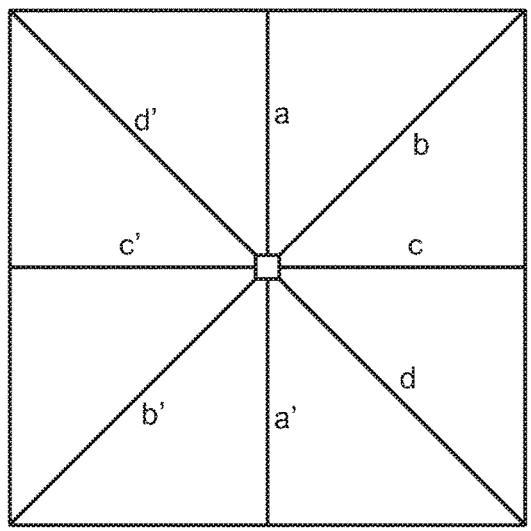
Figure 8D:
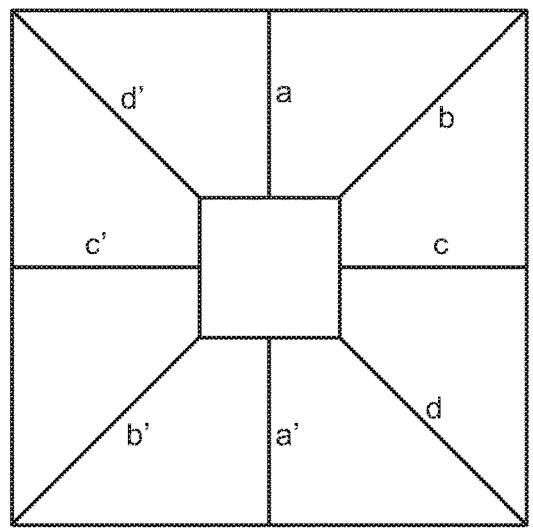

FIGS. 8A-8D are the starting wire or tube materials for the fabrication of the implant as described above for FIGS. 7A-7D but having a rectangular cross-section. In the embodiments of FIGS. 8A-D, the material is removed from the construct to create a traversing radius such that the arms separate from each other and are capable of radial expansion. Accordingly, a cut, or series of cuts, that create a traversing radius is defined as a cut or number of cuts that create one or more radii or one complete diameter such that the arms may expand away to form tissue-engaging regions when the arms expand. If a single cut is made to create two extending arms, the total depth of the cuts must traverse the entire thickness of the rectangular cross section of the construct. Referring to FIG. 8C, the cuts may be made as, for example for a solid construct, for one complete thickness by combining segments a and a'. Three arms would be created by executing cuts at segment a, segment b', and d. Four arms would be created by cuts at segment a, segment a', segment c, and segment c'. Each of the above described configurations would yield an implant where the tissue engaging regions deploy symmetrically or asymmetrically depending on the number of cuts and the desired shape that the implants are heat-set to in the manufacturing process to achieve the desired functional characteristics.

Similarly, a three-armed implant could be created by radially traversing cuts at segment a, segment a', and segment c to create an asymmetric implant. The cut must be deep enough to form the arms when all of the cuts are complete. Referring to FIG. 7B, the cuts need not constitute an entire radius of the width of the construct, but only that width of the solid portion needed to create the expanding arms. Accordingly, cutting the segments a and a' are less than the distance of an entire outer diameter of the construct but are still adequate to create the expanding arms.

Figure 9:
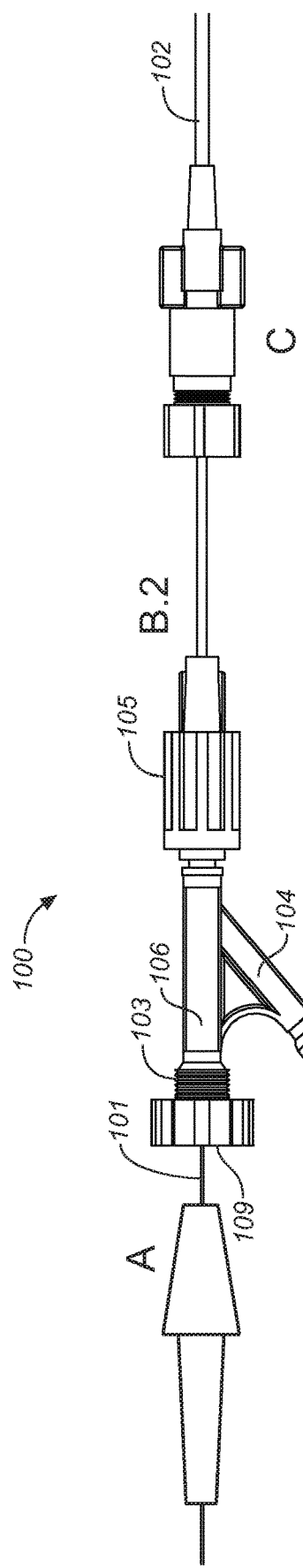
FIG. 9 illustrates the proximal end of the delivery system of the invention including components A, B.1, B.2, and C in combination and with a conventional cystoscope showing placement of an embodiment of a system for deployment of the implant of the invention from a distal end of the delivery system.

Referring to FIG. 9, individual and assembled components A, B.1, B.2 and C of a delivery system 100 of the invention are shown in an operative relationship with a conventional cystoscope 111 (shown in FIG. 10) for placement of an embodiment of the implant of the invention from a distal end of the delivery system 100. Specifically, FIG. 9 at component A is a proximal assembly of the delivery system 100 showing a continuous guide wire or an implant holding wire 101 entering the open proximal port 109 of lumen 106 and proximate to an irrigation port 104 that is in turn proximate to an intermediate coupling 105 that creates a seal to form an intact fluid connection between the irrigation port 104 and the delivery system 102 through a Luer lock 103 and having a configuration for a stopper (not shown) to seal the irrigation port 104.

Figure 10:
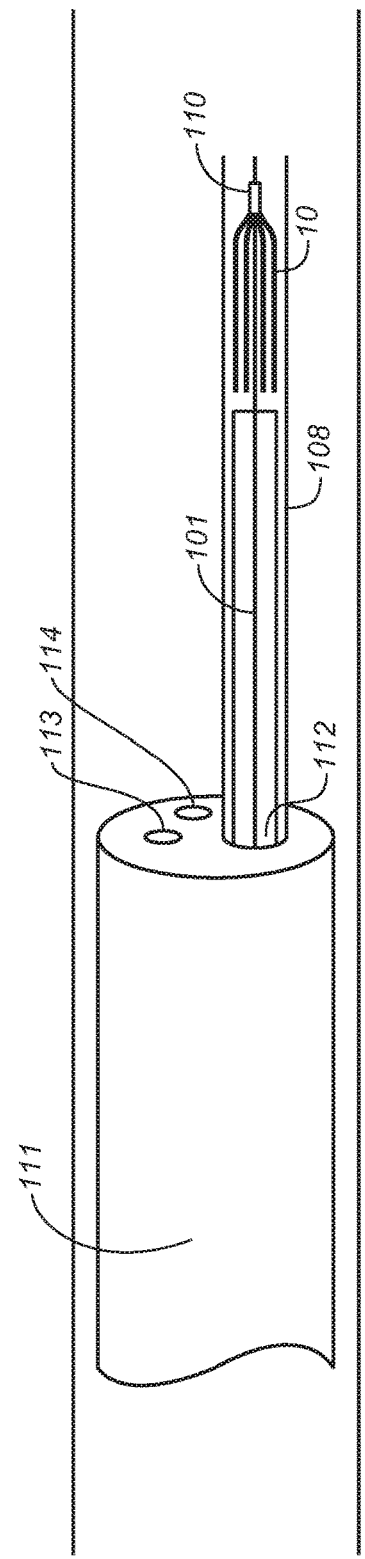
FIG. 10 shows the distal end of a conventional cystoscope of the invention and the distal end of the delivery system sheath, protruding through the instrument or working channel, from the distal end of the cystoscope. The distal end of the delivery system is shown containing an implant of the invention, still maintained within the sheath in a compressed or constrained configuration and at the distal end of the sheath prior to deployment of the implant.

FIG. 10 is a distal end of the outer sheath 108 of the integrated delivery assembly 100 showing the distal end of a conventional cystoscope 111 and the distal end of the delivery sheath 108 protruding from the distal end of the cystoscope 111 and traversing the working channel 112 of the cystoscope 111 and containing an implant 10, still maintained within the compressed configuration and at the distal end of the sheath 108 prior to manual, incremental retraction of the sheath 108 for deployment. The distal end of the continuous guidewire 101 has a pre-dispositioned shape or fixture or tether mechanism 110 to enable controlled and accurate deployment of the expander implant at the target site. This feature on the guidewire or implant holding wire also prevents the implant from deploying prematurely from the distal end of the assembly formed of the outer sheath 108 the implant 10 and the guidewire 101 when the implant 10 is in the compressed configuration. In one embodiment of the guidewire feature, the controlled deployment of the implant 10 is enabled by creating an undulating portion 101a on the guidewire 101 (not shown in the figure). In FIG. 10 the guidewire 101 traverses both the proximal and distal hub 31a, 31b. It will readily be appreciated that any of the implants of the invention described herein can be affixed to the distal end of the delivery system 100 in a collapsed configuration. If the implant contains one or more hub fixtures, for example the hub 11, 21, as illustrated in FIGS. 2A-B and the proximal and distal hub 31a,31b of FIGS. 3A-E, the guidewire 101 preferably traverses the hub for orientation and placement of the implant by the urologist. In other embodiments, the guidewire may be engaged to the implant via tether loop. Following deployment of the implant, the guidewire may be removed to disengage the guidewire from the implant.

FIGS. 11A-C illustrate the incremental, step-wise deployment of the implant 10 as described above. Accordingly, the combination of the deployment system and the implant progress through 3 basic stages: 1) a first stage (FIG. 11A) wherein the implant 10 is maintained in a compressed configuration at the distal end of the delivery system 110 and maintained in a configuration by the structure of the outer sheath 108 (FIG. 11A); 2) a second stage wherein the user begins to push the mandrel forward pushing the implant forward. The outer sheath 108 at this point is only partially withdrawn from about the axial length of the implant 10 (FIG. 11B); and 3) a third stage wherein the mandrel pushes the implant completely out of the outer sheath (FIG. 11C). This allows complete expansion of the implant 10 to the expanded configuration while the implant 10 is still engaged by the guidewire 101, thereby allowing further manipulation of the location and orientation of the implant 110 within the urethra. Following or contemporaneous with release of the implant from the delivery system 100, the implant 10 expands from the collapsed configuration to the expanded configuration followed by withdrawal of the guidewire 101 and final deployment of the implant as represented by FIG. 1. Other deployment mechanisms and embodiments may be conceived and used by those skilled in the art to deploy the implant in the prostatic urethra by retracting the outer sheath 108.

The implant deployment mechanism of the delivery system of invention may have any mechanical expedient (not shown) that allows the physician to actuate a handle in rotary fashion to retract the outer sheath to deploy the implant from the distal end of the delivery system. The handle is adapted to be grasped by hand and rotates around a shaft. Rotation of the handle around the shaft by drawing the handle toward the user engages a gear mechanism, having a fixture attached to the outer sheath.

The delivery system 100 may be fixedly attached to a deployment mechanism such that rotation of the handle causes retraction of the sheath 108 along the length of the hypotube or pusher rod 119. The rotation provides both a first position wherein the implant 10 is fully contained, in the collapsed configuration, within the distal end of the outer sheath 108 and is removably attached to the guidewire 101. Actuation of the handle can be performed in an incremental fashion such that the implant is deployed in stages as described in connection with FIGS. 11A-11C above. In a preferred embodiment, the handle has partial stops at incremental deployment steps for the implant 10. A first incremental stop is a deployment of the implant 110 to an initial stage wherein expansion from the collapsed configuration is begun. A second incremental stop provides deployment of the implant 110 to an intermediate phase wherein the positioning and orientation of the implant can be visually verified. Rotating the handle to the final position completely deploys the implant 110 from the distal end of the outer sheath 108 under visualization.

In use, pursuant to a method of the invention, the delivery system 100 has an overall outer dimension (OD) less than 7 French and is introduced via the working channel 112 of a cystoscope 111, typically having an outer diameter of 17 French. The urologist visualizes the prostatic urethra using the light source 112 and lens 113 integrated into the cystoscope 111 and typically measures the length of the prostatic urethra and evaluates the extent of narrowing of the urethra caused by the BPH condition. From this visualization, the urologist selects the appropriate implant size, and selects from a pre-assembled implant package containing the delivery system 100 with the correctly sized implant 10 already disposed in the collapsed configuration therein. While the distal tip of the cystoscope 111 is located inside the patient's bladder, a saline source is attached to the irrigation port 104 and irrigation is commenced. Under direct visualization, the assembly of the cystoscope 111 and the delivery system 100 is oriented so that the distal end of the cystoscope 100 is placed just proximal to the targeted area at or away from the verumontanum.

The outer sheath 108 is advanced to a position proximal to the bladder neck, and after confirming direct visualization that the implant 110 is proximate to the target portion of the urethra impinged or narrowed by prostatic tissue, the delivery sheath 108 is pushed forward causing the implant 110 to achieve an initial, partially expanded configuration. The forward push of the mandrel is interrupted to verify that the implant is well-positioned and is located in the appropriate target site. After verification, the outer sheath 108 is further withdrawn causing the implant 110 to reach a fully expanded configuration at an intermediate step of the implant 110 deployment, similar to the overall configuration illustrated in FIG. 11C. Once placement, targeting, and orientation are verified by the urologist, the guidewire 101 is withdrawn, followed by withdrawal of the outer sheath 108 and the delivery system 100.

As noted above, the design of the delivery system 100 and the several embodiments of the implant 110, permits an incremental and well-controlled deployment of the implant 110 so that the implant 110 does not "spring open" or "spring forward" prematurely and deploy at in an unsuitable configuration or location away from the target site. By selected and incremental retraction of the outer sheath 108 from an initial position where the implant 110 is partially deployed, to an intermediate position where the implant 110 has completely reached the expanded configuration but is still tethered to the guidewire 101, preferably followed by verification of the size of the implant in the placement within the prostatic urethra. Removal of the guidewire 101 in the outer sheath 108 completes a multi-step deployment process. The guidewire avoids inadvertent, premature deployment of the implant 110 or misplacement of the implant 10, which can be irreversible and require removal of the implant 110, and repeat treatment by deploying a new implant using a new deployment or delivery system 100.

The methods of the invention include deploying an implant into the urethra wherein the implant having two or four or a greater number of tissue engaging regions to retract at least two discrete regions of enlarged prostatic tissue at the surface of tissue of the lobe in a patient in need thereof. A radial force is exerted at at least the two discrete regions and each region is each contacted along the interior wall of the urethra. In some embodiments, the force is exerted on the tissue along an axis perpendicular to an axis that runs the linear length of the urethra and which traverses the central axis of the implant of the invention. The methods include a procedure to remove the implant of the invention, upon further diagnosis of BPH or LUTS in a patient, and which is based on the design of the invention. In the removal process, the most proximal portion of the implant is accessed by a wire or suture extending from an opening at the distal end of a retrieval tube and the implant is engaged proximate to the hub and drawn into the retrieval tube, thereby reversing the deployment process and returning the implant from the expanded to the confined configuration. When the implant is placed such that the hub is more distal than the tissue engaging portions of the implant based on the initial clinical judgment and deployment by the physician, the implant may be pushed distally into the bladder and re-oriented such that the hub can be engaged in the implant drawn into the distal end of the retrieval tube.

A method to alleviate clinical symptoms of benign prostatic hyperplasia is performed by placing the implant, apart from and optionally proximal of the ejaculatory ducts, by-advancing a deployment catheter having a proximal end and a distal end through a working channel of a standard urology cystoscope to position the distal end of the catheter containing the implant at a point between the bladder neck and the external sphincter. Once the distal end of the delivery system reaches the target site, the implant is deployed whereupon it expands from a compressed configuration to an expanded configuration to engage hyperplasic prostate tissue. During the deployment, proximal and distal hubs of the implant, which are in a substantially linear configuration when the implant is maintained in the collapsed configuration and while the catheter is advanced through the working channel. In this configuration, the arms are maintained in a substantially parallel condition being relatively aligned with one another within the confines of the inner diameter of the delivery system catheter.

During deployment, the expansion from the initial confined configuration to the expanded configuration features characteristic changes in the orientation of the structures of the implant. In all of the embodiments, the arms of the implants that are comprised of tissue-engaging regions expand to engage the enlarged prostatic tissue. Portions of the implant may assume a different shape transforming from substantially linear to curvilinear or a sigmoid form depending on the design and orientation of the implant upon deployment.

in the embodiments describing above having a proximal and a distal hub interconnected by a plurality of arms, the linear distance between the proximal and the distal hubs is changed from a first position in the collapsed configuration to a second position in the expanded configuration where the distance between the hubs is reduced in the second position. In embodiments where a hub is connected to first and second transitional region of each of the arms converts, the transitional regions transform from a substantially linear to a curvilinear form, wherein the first transitional region is distal to the proximate hub and connected thereto and the second transitional region is proximal to the distal hub and connected thereto. A tissue-engaging segment of each arm that is preferably centrally disposed in the length of the implant expands away from a central axis of the retrievable implant to engage enlarged prostate tissue along at least a portion of the length of the central tissue-engaging segment. In some embodiments, the length of the tissue-engaging region that engages the prostate tissue is substantially linear.

The expansion from the collapsed to the expanded configuration produces an integral connection between a solid circumferential region of each of the proximal and distal hubs and the central tissue-engaging segment of the plurality of arms. During deployment, the tissue engaging portions are preferably oriented such that the plurality of 4 arms do not engage inter-lobular grooves of the prostate.

The methods of the invention also include a separate procedure for retrieving the implant through the working channel of the cystoscope. The step of retrieving the implant can be performed by engaging any portion of the implant that permits the implant to be drawn into the distal end of a retrieval system where the implant reverts from an expanded configuration to a collapsed configuration. The implant may be engaged at any point on the structure of the implant or by engaging a fixture on the proximal hub and retracting the implant into the distal end of a retrieval catheter. Engaging in the implant may be achieved by using a retrieval wire that has a specially configured distal end that loops back on itself for secure engagement of the implant.

The invention also includes the configuration wherein catheter for delivery of a retrievable implant in a collapsed configuration is delivered through the working channel of a flexible cystoscope and placed in an expanded configuration in a prostatic urethra narrowed by hyperplasia where the combination is an outer sheath for constraining the retrievable implant at a distal end, a pusher or push rod sized to traverse the length of an inner lumen of the catheter and having a fixture at the distal end thereof to engage the proximal portion of the retrievable implant and to advance the retrievable implant distally relative to the catheter to deploy the implant, and a delivery wire to assist accurate placement of the retrievable implant. Preferably, the outer diameter of the delivery catheter is less than 9 French and optionally includes: a fluid communication lumen, a camera, and scope, or visualization apparatus for direct imaging during deployment of the implant. The device can include radiographic, fluoroscopic, or other imaging markers to assist in positioning of the delivery system or the implant.

The invention also includes unique advantages in the structure and performance of the implant that is derived from the selection of the starting materials and the fabrication processes described herein. In some embodiments, the implant is made from a unitary body of shape-memory or super-elastic material by the selective removal of material along a selected length of the elongated and unitary body and traversing a diameter thereof, wherein the selected length is less than the total length of the elongated and unitary body used to fabricate the implant such that the resulting structure may be either symmetric or asymmetric about a central axis considered as an imaginary line down the length of the implant. Although the embodiments fabricated from a single tube can be considered integrally connected and unitary, because they are formed from a continuous piece of material, individual structures of the implant can be welded together to yield any configuration. Where material is removed from the tube, essentially any configuration can be created by known micro-machining techniques with the only constraint being that enough material must be removed from a length along the linear length of the tube from which the implant is fabricated such that enough material is removed to form the arms. This parameter can be described as the need to traverse a diameter of the construct from which the implant is manufactured such that the cuts must are collectively deep enough to at least cut through the solid portion of the tube in the middle of a cross section of the tube so that the arms can move away from each other. If the tube is solid, such a distance is the entire diameter collectively to yield a "quadrant," but if hollow then through to the hollow portion to form an "arc."

The methods are driven by the physiology of the individual patient and are at the discretion of the urologist, although the procedures generally include the steps of advancing a deployment catheter having a proximal end and a distal end through a working channel of a urology cystoscope to position the distal end of the catheter at a point between the bladder neck and the external sphincter. Once in the proper position and orientation, the urologist deploys the implant from the distal end of the catheter to expand the implant from a collapsed to an expanded configuration. Deployment of the implant causes the tissue-engaging regions of the implant to engage enlarged prostate tissue along a length of a plurality of elongate arms of the implant. Some of the embodiments have the configuration where the tissue-engaging regions are disposed on the arms that connect the two hubs and in this configuration a length of the arms forms an elongated structure such that a series of substantially linear arrangement arms go from a configuration being constrained by the catheter in the collapsed configuration to an expanded configuration wherein each of the arms is integrally connected at both ends to the hubs.

Because of the design of the two-hub embodiment of the implant, the expansion of the plurality of arms during deployment causes the proximal hub and the distal hub to move linearly toward each other along an axis connecting the hubs while the plurality of arms expand to engage the enlarged prostate tissue. The result is that the distance between the hubs in the expanded configuration is less than the distance in the collapsed configuration.

The arms can be described as having transitional regions that are integrally formed with each hub such that a first transitional region is integrally formed proximate to one hub and a second transitional region is integrally formed proximate to the second hub with the tissue-engaging regions of the plurality of arms disposed therebetween. These first and second transitional regions convert from a substantially linear form to a curvilinear form when the implant converts from the collapsed to the expanded configuration.

The implant is designed so that the radial forces exerted by the implant are applied directly to the prostate lobes rather than an orientation wherein the tissue engaging regions are confined to the intralobular grooves. For this reason, the method of the invention includes taking advantage of the design of the implant to position the device for deployment such that at least 2 of the plurality of arms do not engage inter-lobular grooves of the patient's prostate.

As noted above, important part of the design features of the present implant is the ability to retrieve the implant when the clinical discretion of the urologist so indicates. Typically, the retrieval process includes the step of retrieving the implant through the working channel of the cystoscope. Specifically, the urologist captures the implant by engaging either the body of the implant or a dedicated structure of the implant and inserting the implant into the distal end of a retrieval catheter, usually by drawing the implant into the catheter, whereby the implant reverts from the expanded to the collapsed configuration. The implant is designed so that the retrieval process can involve engaging the body of the implant at a dedicated fixture or simply by a grasper that engages a cylindrical portion of a hub that can be specifically modified to form a loop at the most proximal or most distal portion of the implant or both. Depending on the physiology of the individual patient, the retrieval may also occur by advancing the implant into the bladder while it is in the expanded or partially expanded configuration followed by drawing the implant into the distal end of the retrieval catheter for removal.

While the retrieval method is preferably comprised of engaging the implant at the target site at which the implant was originally deployed and withdrawing the implant directly approximately through the urethra, the retrieval can be achieved by advancing implant distally into the bladder prior to removal.

The Examples disclosed above are merely intended to illustrate the various utilities of this invention. It is understood that numerous modifications, variations and combinations of functional elements and features of the present invention are possible in light of the above teachings and, therefore, within the scope of the appended claims, and the present invention may be practiced otherwise than as particularly disclosed.

All patents and publications are herein incorporated for reference to the same extent as if each individual publication was specifically and individually indicated to be incorporated by reference. It should be understood that although the present invention has been specifically disclosed by preferred embodiments and optional features, modification and variation of the concepts herein disclosed may be resorted by those skilled in the art, and that such modifications and variations are considered to be within the scope of this invention.

What is claimed is:

1. A retrievable implant sized and configured for placement in a prostatic urethra narrowed by enlarged tissue and expandable between a collapsed configuration and an expanded configuration comprising:
 a proximal hub and a distal hub separated along a longitudinal axis by a first distance in the collapsed configuration, the proximal hub having a distal end and a proximal end, the distal hub having a distal end and a proximal end; and
 a plurality of arms connecting the distal end of the proximal hub and the proximal end of the distal hub, each of the plurality of arms having an equal length and having a length equaling the first distance when in the collapsed configuration, wherein in the expanded configuration in the prostatic urethra, the proximal hub and the distal hub are separated by a second distance when the arms are deployed outward and in a predetermined shape to retract the enlarged tissue, and further wherein in the expanded configuration, each of the deployed arms has a total tissue-engaging surface length that exerts a force between 5 and 30 N on the enlarged tissue in a direction perpendicular to the longitudinal axis such that the total tissue-engaging surface length is less than or equal to the second distance and the distal end of the proximal hub is positioned proximal to the total tissue-engaging surface length and the proximal end of the distal hub is positioned distal to the total tissue-engaging surface length.

2. The retrievable implant of claim 1, wherein each of the proximal hub and the distal hub are disposed about a central axis of the retrievable implant.

3. The retrievable implant of claim 1, wherein each of the proximal hub and the distal hub are disposed eccentrically relative to a central axis of the retrievable implant.

4. The retrievable implant of claim 1, wherein each of the proximal hub and the distal hub are comprised of a circumferentially solid region.

5. The retrievable implant of claim 1, wherein each hub is integrally formed with the plurality of arms and each arm is connected to each hub at a transitional region that is substantially linear in the collapsed configuration and curvilinear in the expanded configuration.

6. The retrievable implant of claim 5, wherein each arm is comprised of a central tissue-engaging region.

7. The retrievable implant of claim 6, wherein the tissue engaging region has a substantially linear segment.

8. The retrievable implant of claim 7, wherein the tissue-engaging region has a linear segment length in the expanded configuration of at least 1 mm.

9. The retrievable implant of claim 5, wherein in the expanded configuration the predetermined shape has a diameter defined by tissue-engaging regions of the plurality of arms and wherein the retrievable implant has an outer diameter of at least 8 millimeters.

10. The retrievable implant of claim 1, wherein in the collapsed configuration the retrievable implant has an overall diameter less than 7 French.

11. The retrievable implant of claim 1, wherein each of the proximal hub and the distal hub is cylindrical and is comprised of a centrally disposed opening traversing the length thereof.

12. The retrievable implant of claim 1, wherein in the expanded configuration: a first pair of the plurality of arms is disposed in a first plane containing the first pair of arms and traversing the proximal and the distal hub and a second pair of the plurality of arms is disposed in a second plane containing the second pair of arms and traversing the second pair of arms, wherein the first plane and the second plane are perpendicular.

13. The retrievable implant of claim 1, wherein either of the proximal hub or the distal hub or both has an attachment proximal to a solid circumferential region of either hub that is integrally connected thereto and has an opening in the attachment to facilitate retrieval of the implant.

* * * * *